United States Patent
Wan et al.

(10) Patent No.: US 10,368,885 B2
(45) Date of Patent: Aug. 6, 2019

(54) SUCTION EVACUATION SHEATH

(71) Applicants: Shaw P. Wan, Norwood, NC (US); Guohua Zeng, Guangzhou (CN)

(72) Inventors: Shaw P. Wan, Norwood, NC (US); Guohua Zeng, Guangzhou (CN)

(73) Assignee: Well Lead Co., Ltd. (CN)

( * ) Notice: Subject to any disclaimer, the term of this patent is extended or adjusted under 35 U.S.C. 154(b) by 584 days.

(21) Appl. No.: 15/061,428

(22) Filed: Mar. 4, 2016

(65) Prior Publication Data
US 2017/0252051 A1  Sep. 7, 2017

(51) Int. Cl.
| | |
|---|---|
| A61B 17/22 | (2006.01) |
| A61B 17/221 | (2006.01) |
| A61B 17/225 | (2006.01) |
| A61B 17/00 | (2006.01) |

(52) U.S. Cl.
CPC .......... *A61B 17/221* (2013.01); *A61B 17/225* (2013.01); *A61B 2017/00946* (2013.01); *A61B 2017/22051* (2013.01); *A61B 2017/22069* (2013.01); *A61B 2017/22079* (2013.01); *A61B 2217/005* (2013.01); *A61B 2217/007* (2013.01)

(58) Field of Classification Search
CPC .............. A61M 1/0058; A61M 1/0033; A61M 1/0035; A61M 1/0037; A61M 1/0039; A61M 1/0041; A61M 1/0047; A61B 17/22; A61B 17/221; A61B 17/22031; A61B 2017/22038; A61B 2017/22079; A61B 2217/005; A61C 17/0208; A61C 17/043
See application file for complete search history.

(56) References Cited

U.S. PATENT DOCUMENTS

| | | | | |
|---|---|---|---|---|
| 5,419,774 | A * | 5/1995 | Willard | A61B 17/3207 604/22 |
| 5,971,938 | A * | 10/1999 | Hart | A61B 17/22031 600/562 |
| 6,599,237 | B1 * | 7/2003 | Singh | A61B 1/0008 600/114 |
| 6,997,867 | B2 * | 2/2006 | Soble | A61B 1/005 600/121 |
| 2004/0019358 | A1 * | 1/2004 | Kear | A61B 17/22031 606/127 |

(Continued)

*Primary Examiner* — Ryan J. Severson
*Assistant Examiner* — Christian D Knauss
(74) *Attorney, Agent, or Firm* — Blake E. Vande Garde; Erickson Kernell IP, LLC

(57) ABSTRACT

A device for removing a stone, a stone fragment, or a foreign body from a patient comprising a suction evacuation assembly which includes a primary sheath with a flexible end, an obturator releaseably secured to the sheath, a side arm emanating from the primary sheath, a deflection mechanism which is operationally associated with the flexible end of the sheath and a secondary sheath with a dual lumen and an oblong shape wherein the dual lumen allow passage of surgical instruments and irrigation fluid and wherein the oblong shape provides for adequate space for the egress of stone fragments and fluid through the primary and/or secondary sheath, wherein the obturator is withdrawn from the primary sheath and the secondary sheath is inserted into the primary sheath and into the patient in order to facilitate the removal of the stone, stone fragment or foreign body.

23 Claims, 16 Drawing Sheets

(56) References Cited

U.S. PATENT DOCUMENTS

2004/0204629 A1* 10/2004 Knapp .................. A61B 1/307
                                                    600/156
2015/0305759 A1* 10/2015 St. George ............... A61B 1/07
                                                    600/135

* cited by examiner

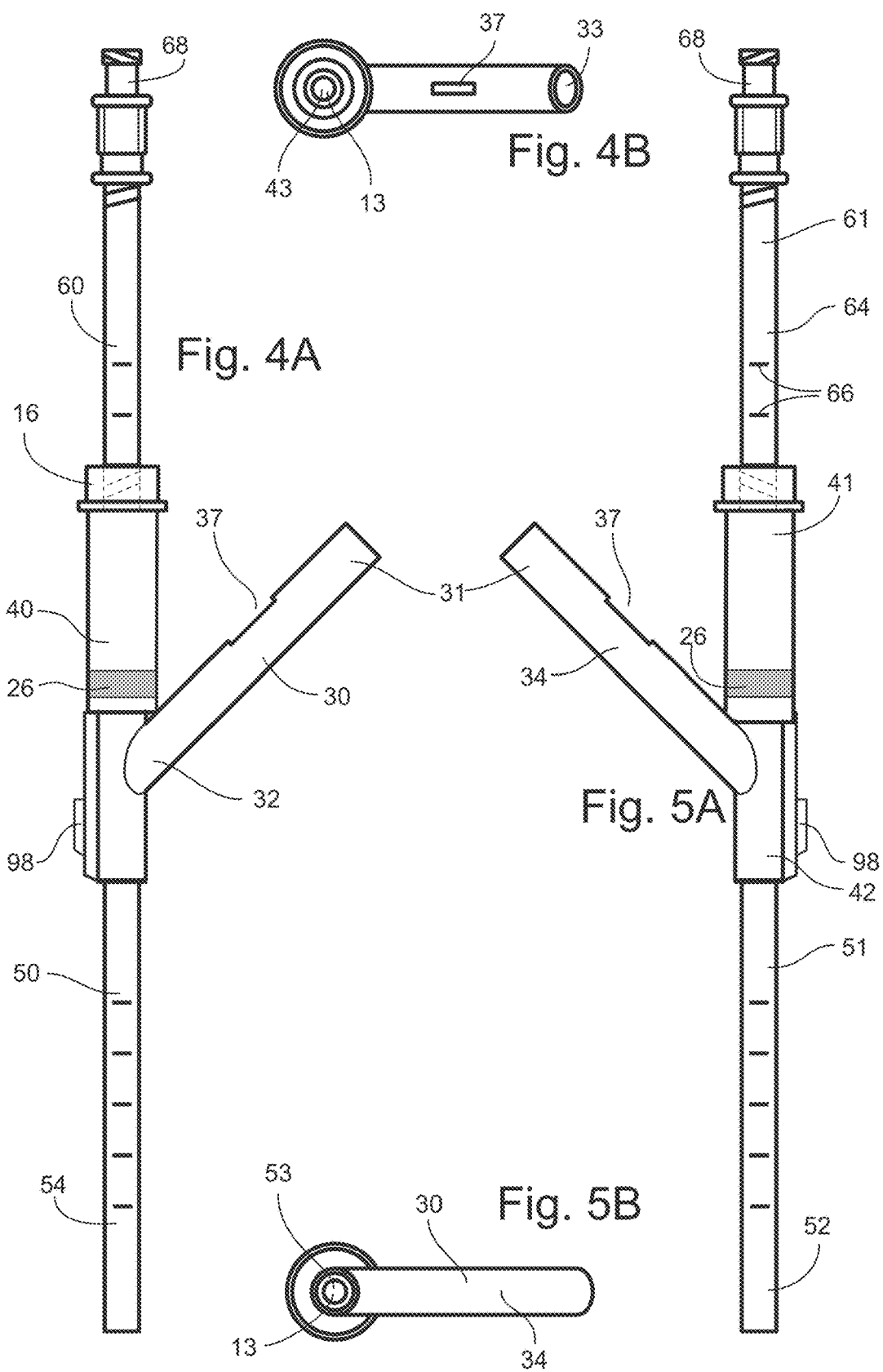

SUCTION EVACUATION SHEATH

FIELD OF THE INVENTION

A surgical device used to retrieve stones from a patient's body is disclosed herein below.

BACKGROUND OF THE INVENTION

Kidney stones have plagued mankind for ages. Complications resulting from the presence of stones in the urinary tract often require surgical intervention to remedy the problem. A patient will require several days in the hospital to recover from a typical surgical procedure to remove a stone wherein a surgeon incises a patient's abdomen in order to remove the stone. The use of less invasive stone retrieval devises has decreased the suffering and recovery time required by a patient. Due to the unique structure of renal anatomy, it is difficult to reach some of the calyces during an endoscopic intra-renal surgery. This is especially true for the lower pole calyces. Unfortunately, even if access to the calyx is achieved during a surgical procedure to remove a stone and the stone is effectively crushed, it is still very difficult to remove the fragments from the calyx. This results in the patient having to pass the fragments on their own which both prolongs the treatment time and the suffering and discomfort experienced.

The stone retrieval devices known in the art fail to perform adequately, thus, there is significant room for improvement. The stone retrieval device disclosed below is an improvement over those known in the art.

SUMMARY OF THE INVENTION

A device for removing a foreign body from a patient comprising a suction evacuation assembly which includes a primary sheath with a flexible end, an obturator releaseably secured to the sheath, a side arm emanating from the primary sheath, a deflection mechanism which is operationally associated with the flexible end of the sheath and a secondary sheath with a dual lumen and an oblong shape wherein the dual lumen allow passage of surgical instruments and irrigation fluid and wherein the oblong shape provides for adequate space for the egress of stone fragments and fluid through the primary and/or secondary sheath, wherein the obturator is withdrawn from the primary sheath and the secondary sheath is inserted into the primary sheath and into the patient in order to facilitate the removal of the stone, stone fragment or foreign body.

Whereas this device was initially developed for the treatment of stone disease; using the same principle, it soon becomes apparent that this device is also applicable for the removal of a foreign body or bodies in the body cavity or lumen and can be used for tissue ablation.

DESCRIPTION OF THE DRAWINGS

For the purpose of illustrating the invention, there is shown in the drawings a form that is presently preferred; it being understood, however, that this invention is not limited to the precise arrangements and instrumentalities shown.

FIG. 4A is a front view of one embodiment of the present invention.

FIG. 4B is a top-down view of one embodiment of the present invention.

FIG. 5A is a back view of one embodiment of the present invention.

FIG. 5B is a bottom-up view of one embodiment of the present invention.

DESCRIPTION OF THE INVENTION

Figure 1:
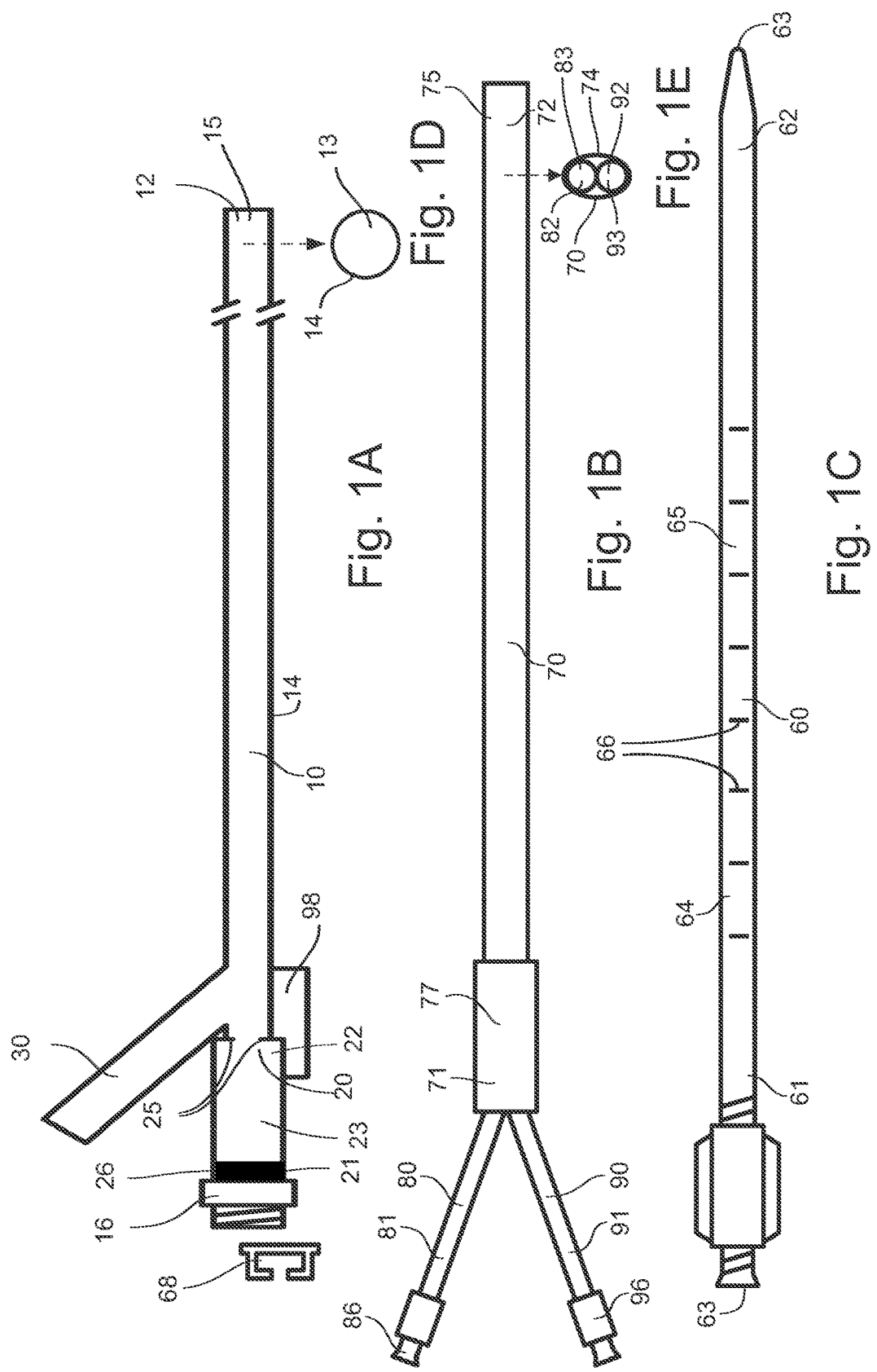
FIG. 1A is a front view of one embodiment of the present invention.
FIG. 1B is a front view of one embodiment of the present invention.
FIG. 1C is a front view of one embodiment of the present invention.
FIG. 1D is a cut-through view of one embodiment of the present invention.
FIG. 1E is a cut-through view of one embodiment of the present invention.
Figure 2:
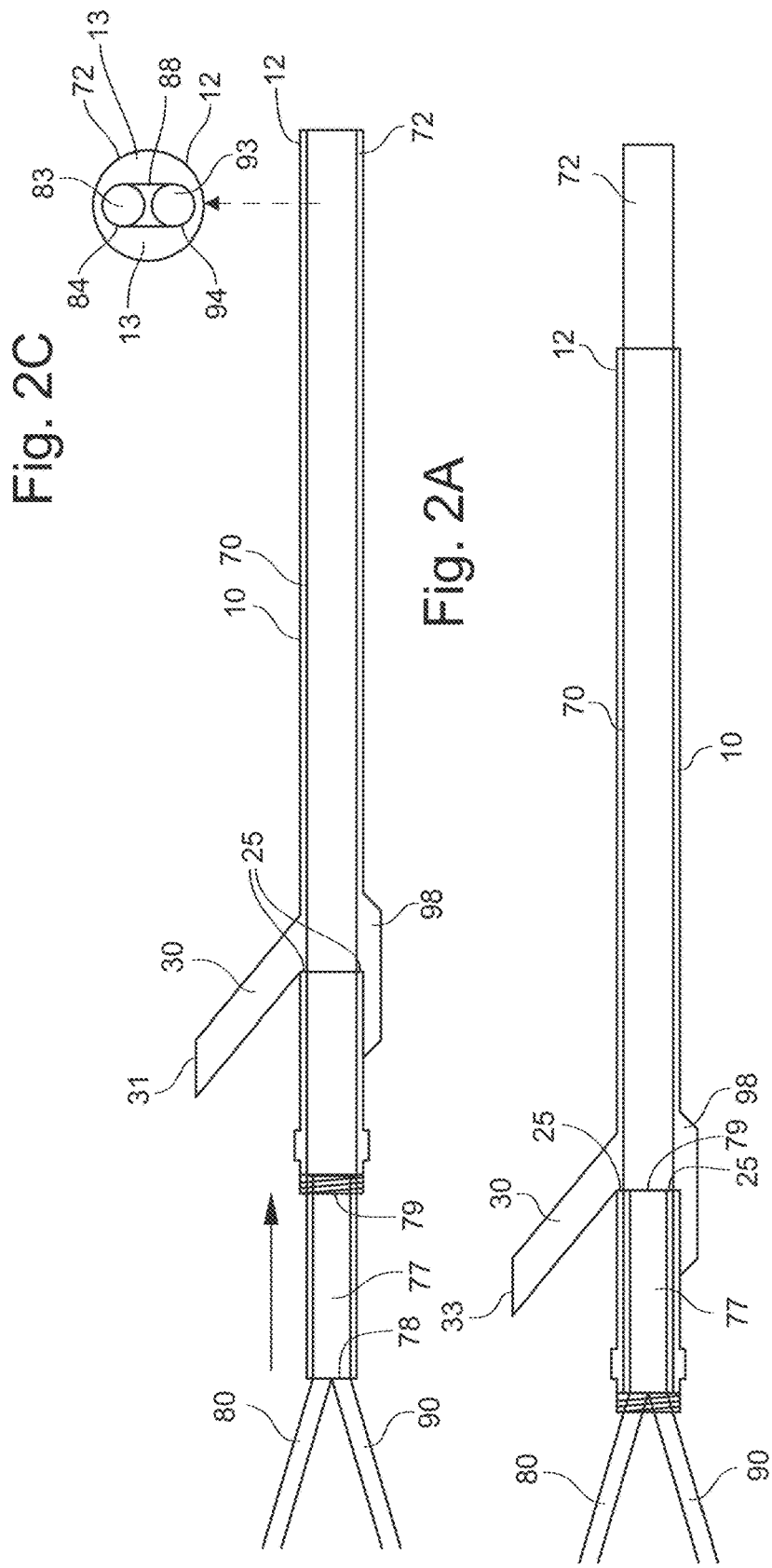
FIG. 2A is a front cut-through view of one embodiment of the present invention.
FIG. 2B is a front cut-through view of one embodiment of the present invention.
FIG. 2C is a cut-through view of one embodiment of the present invention.
Figure 3:
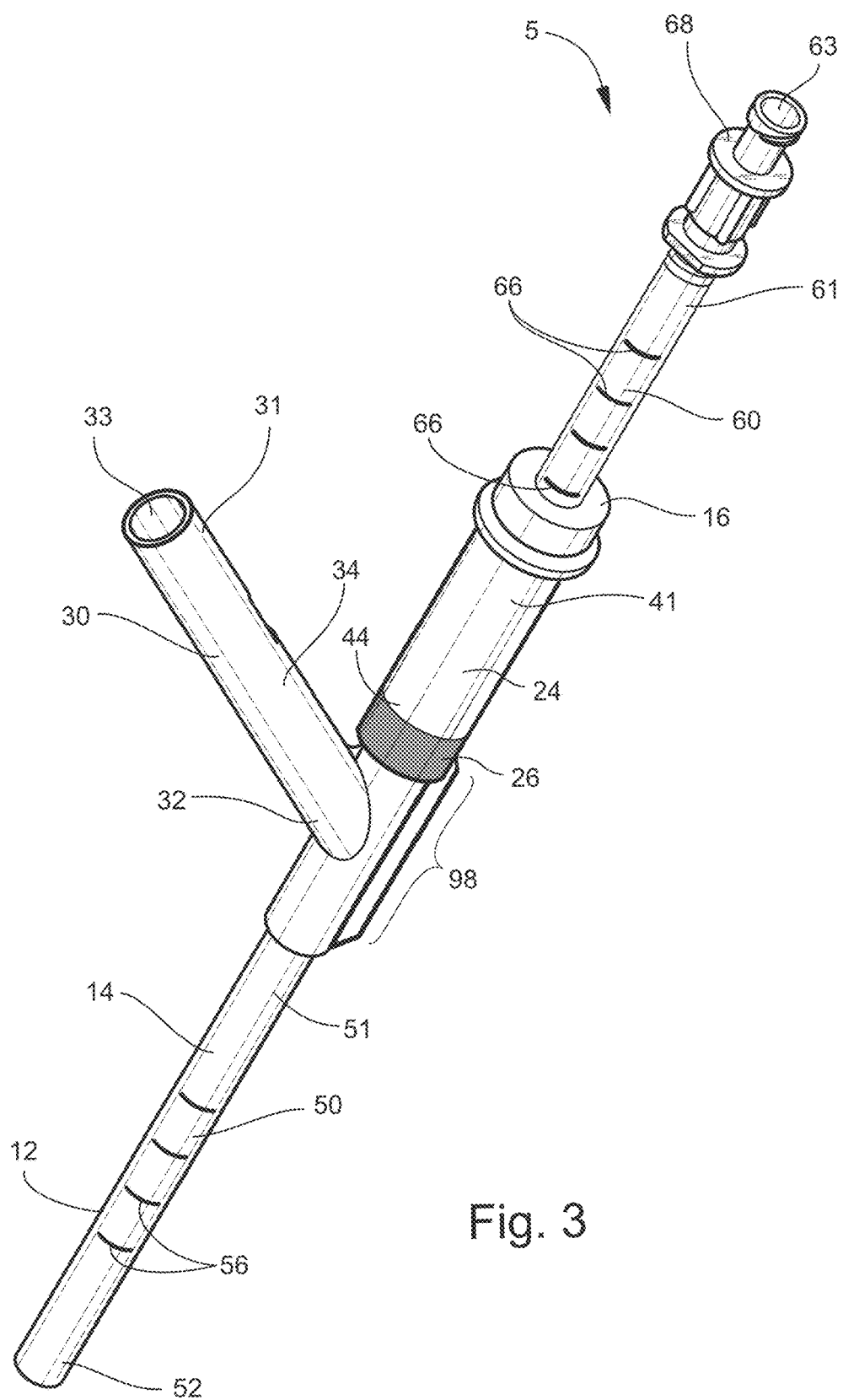
FIG. 3 is a perspective view of one embodiment of the present invention.
Figure 6:
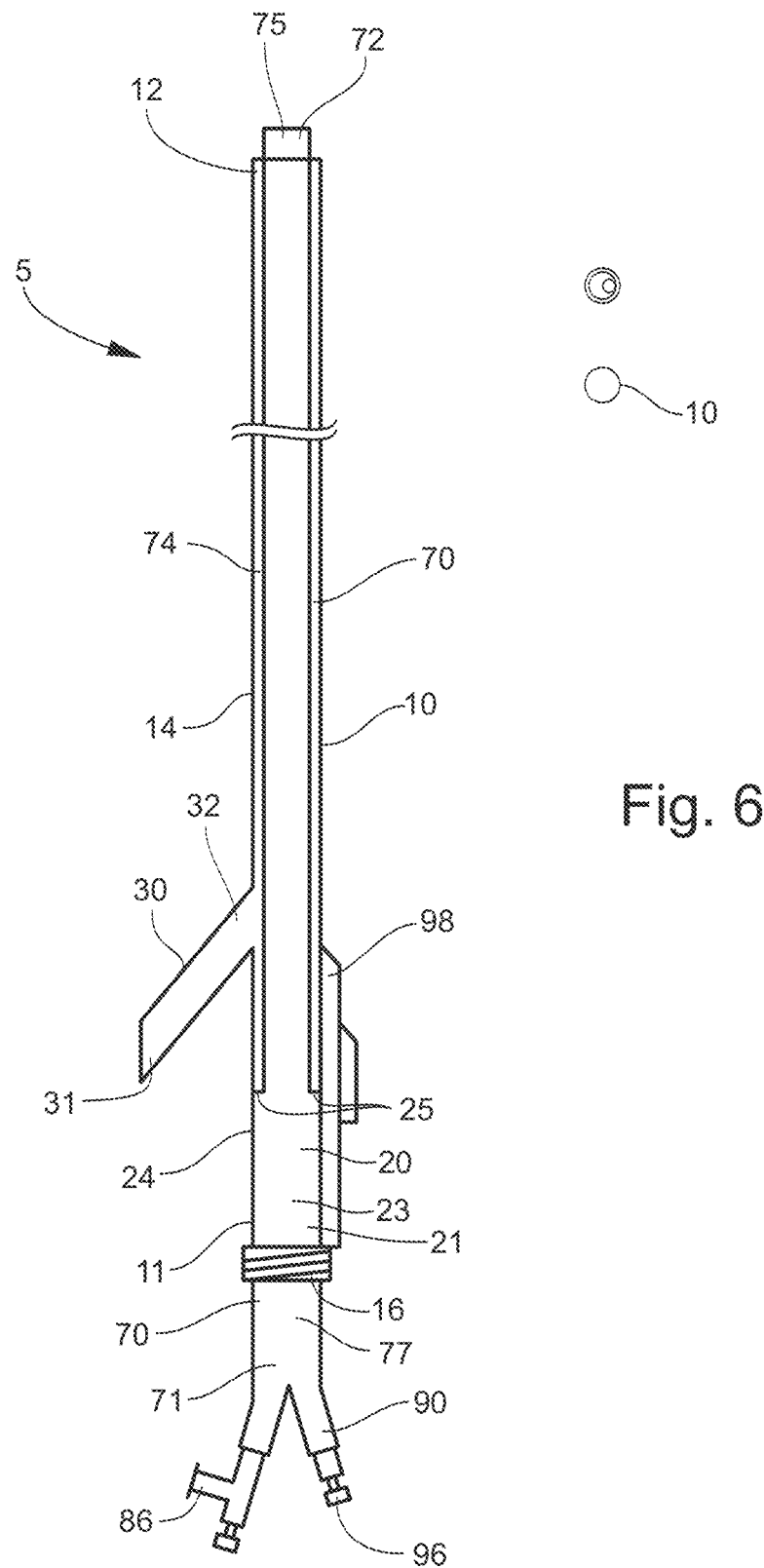
FIG. 6 is a front view of one embodiment of the present invention.
Figure 7:
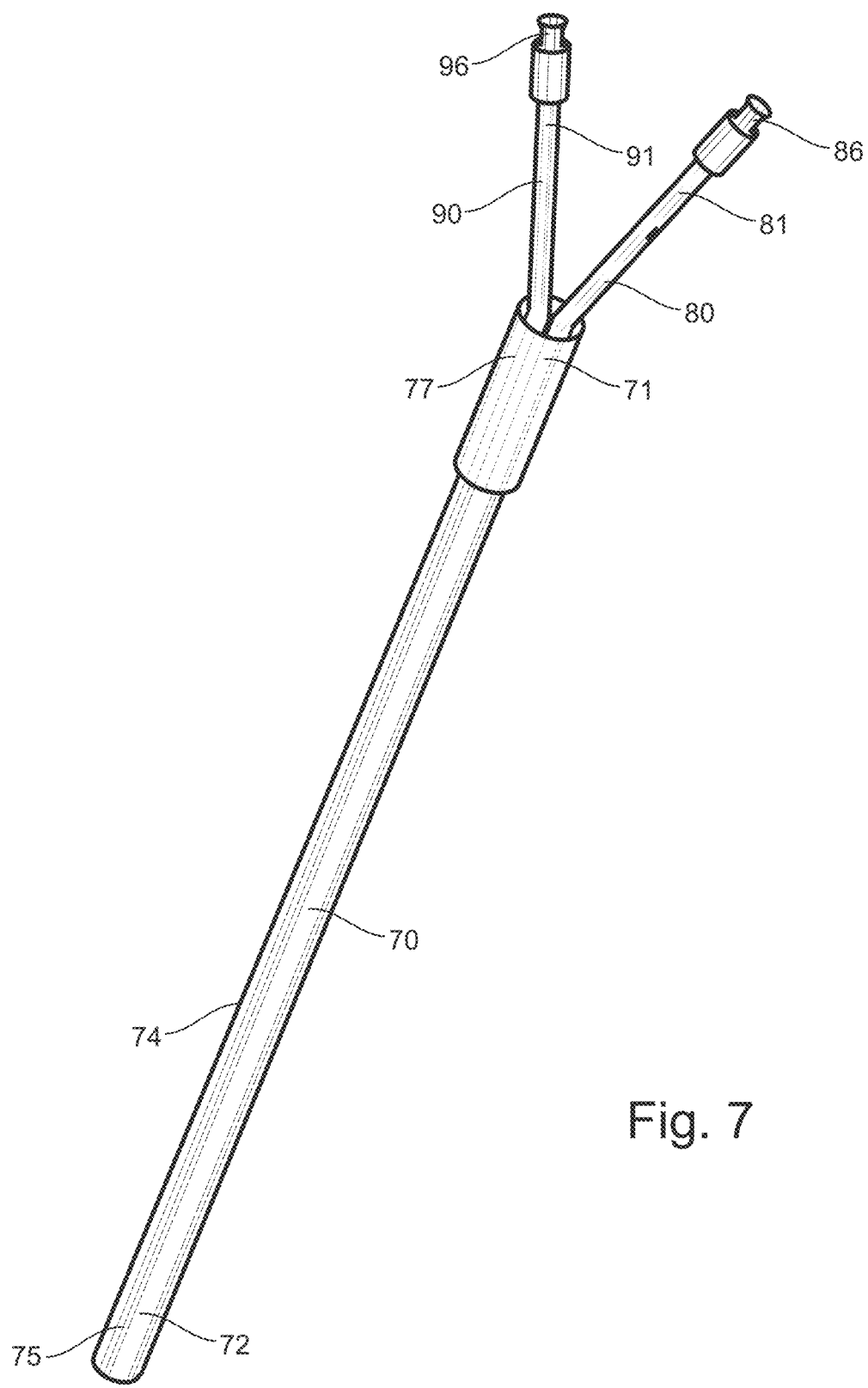
FIG. 7 is a perspective view of one embodiment of the present invention.
Figure 8A:
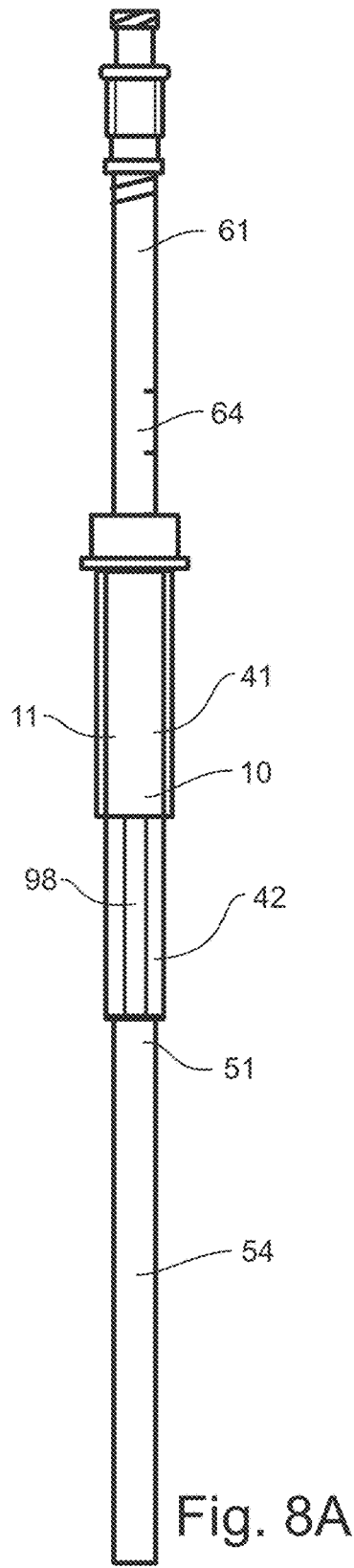
FIG. 8A is a side view of one embodiment of the present invention.
Figure 8B:
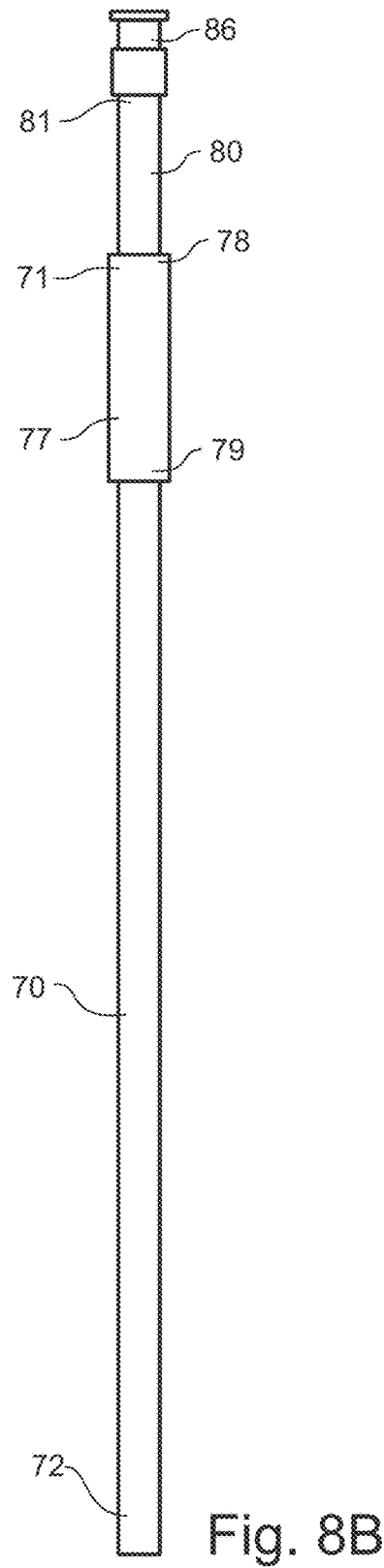
FIG. 8B is a side view of one embodiment of the present invention.
Figure 9A:
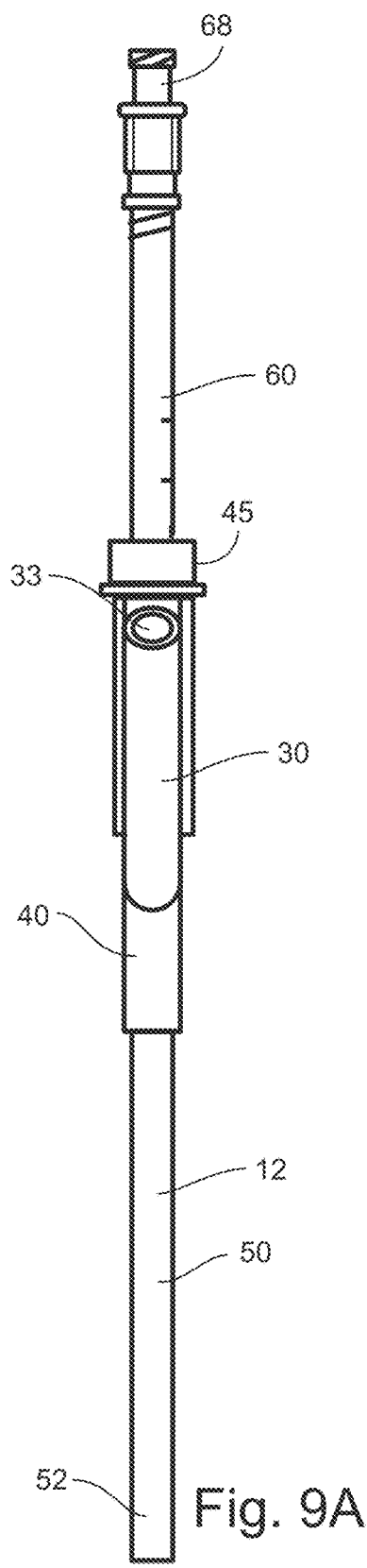
FIG. 9A is a side view of one embodiment of the present invention.
Figure 9B:
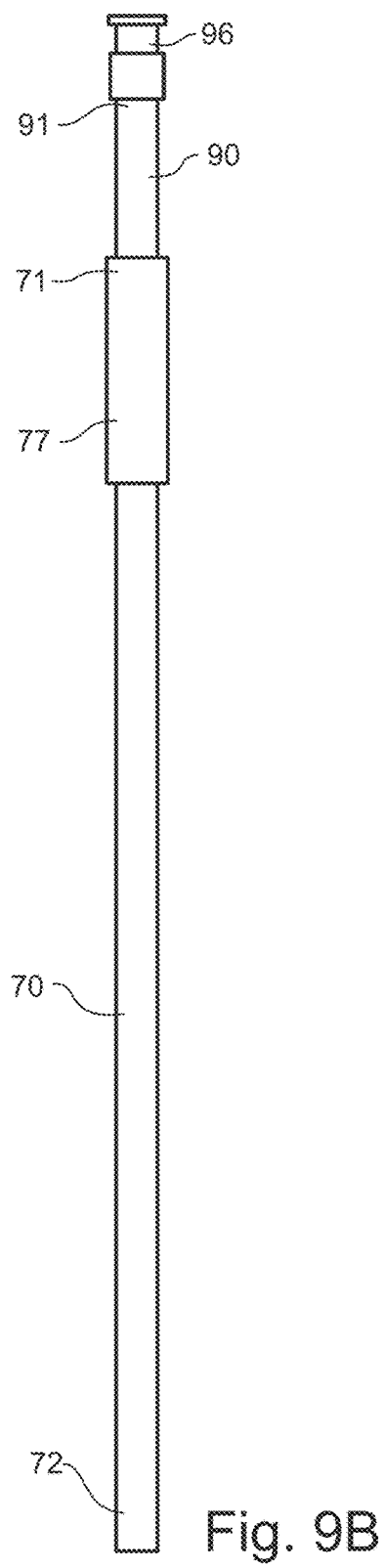
FIG. 9B is a side view of one embodiment of the present invention.
Figure 10A:
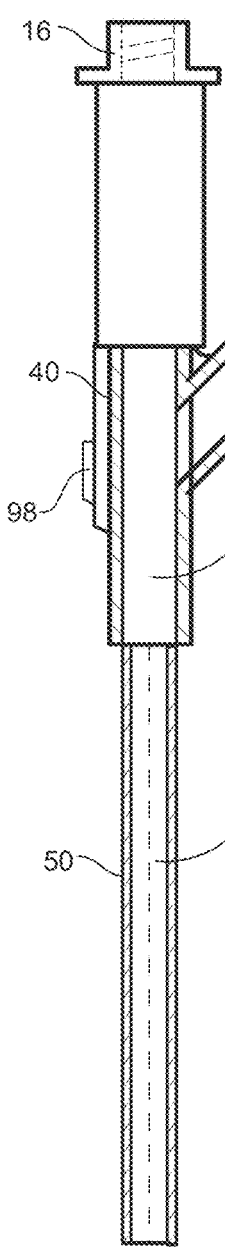
FIG. 10A is a side cut-through view of one embodiment of the present invention.
Figure 10B:
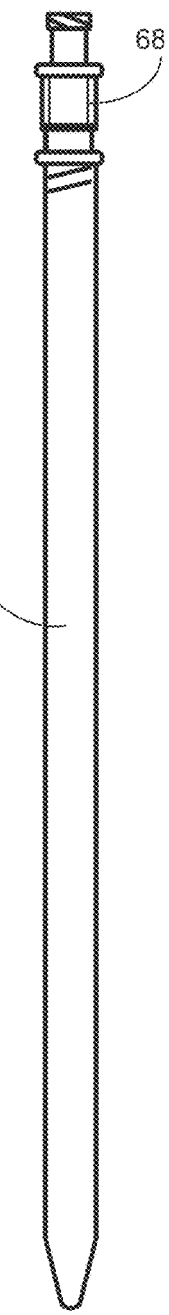
FIG. 10B is a side cut-through view of one embodiment of the present invention.
Figure 10C:
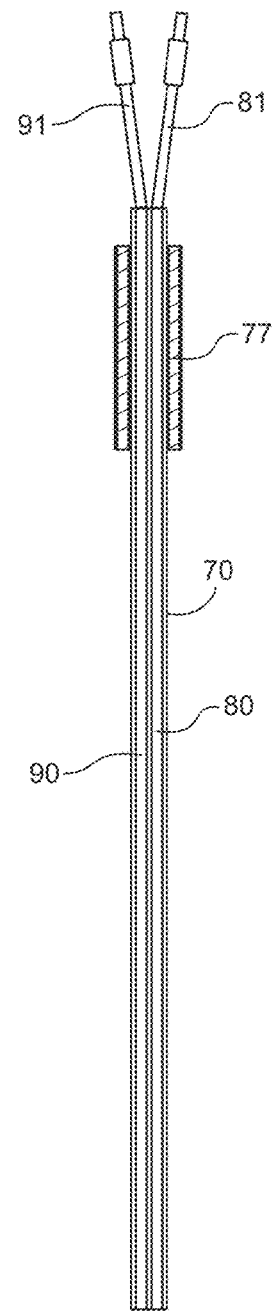
FIG. 10C is a side cut-through view of one embodiment of the present invention.
Figure 11:
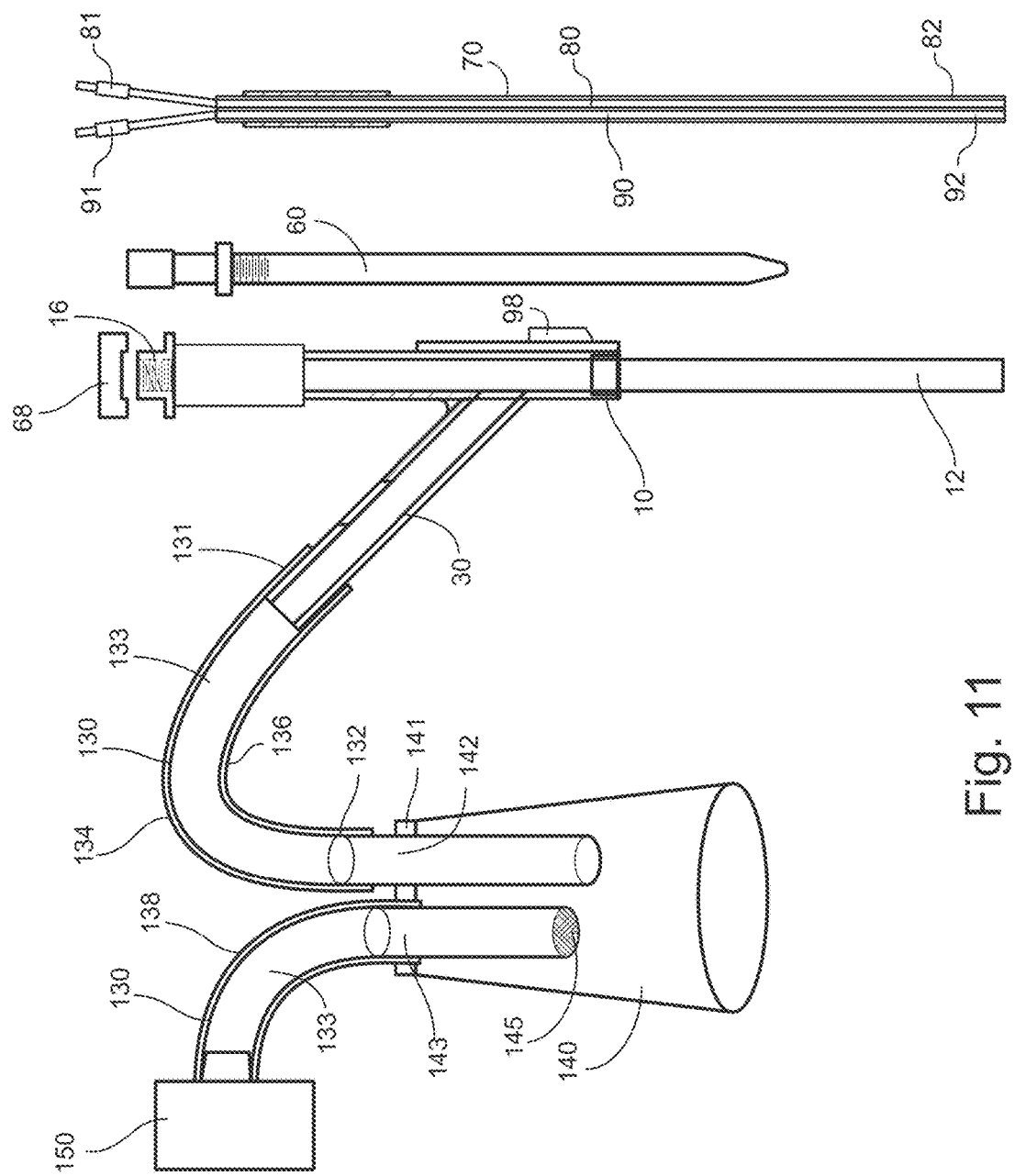
FIG. 11 is a cut through view of one embodiment of the present invention.
Figure 12:
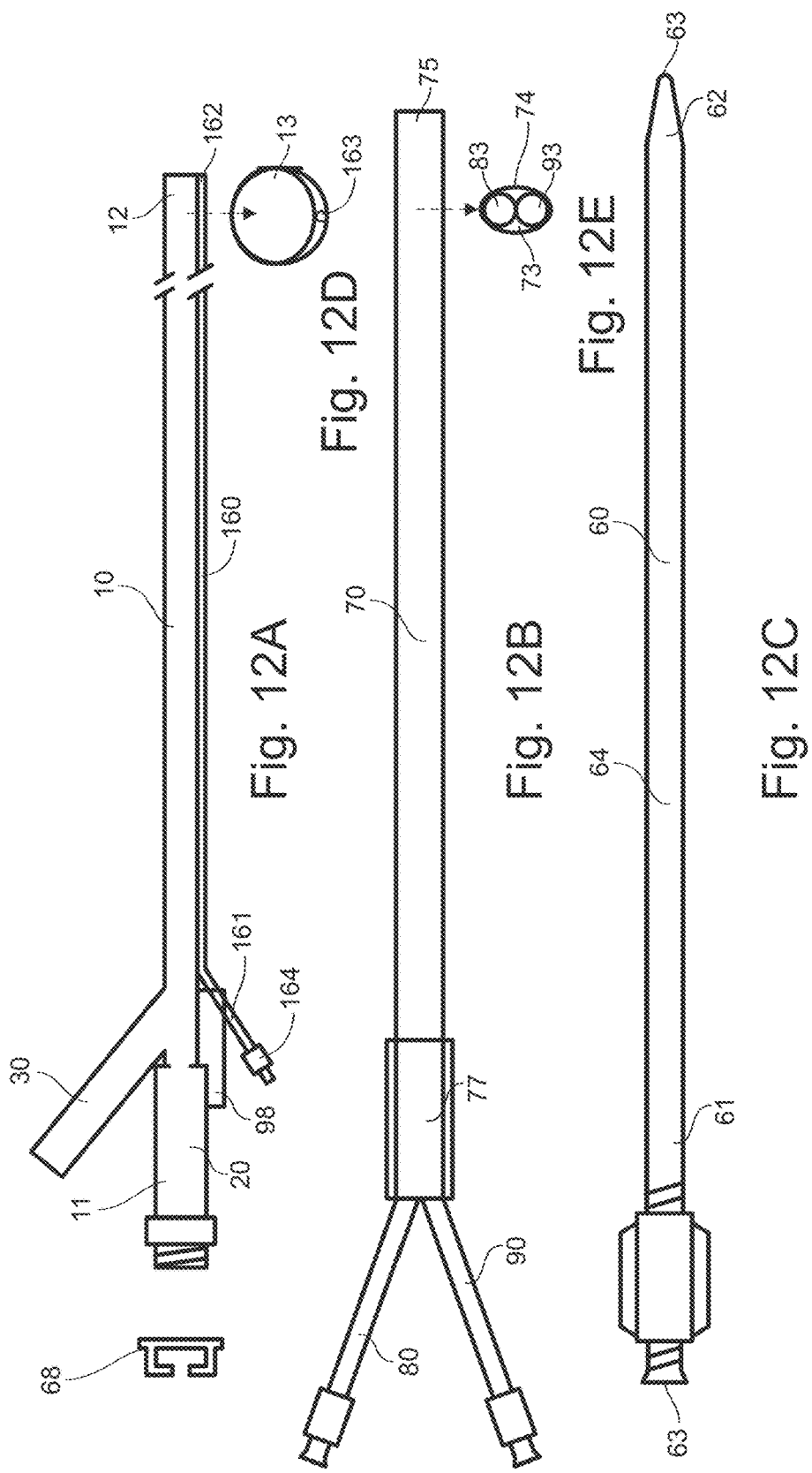
FIG. 12A is a front view of one embodiment of the present invention.
FIG. 12B is a front view of one embodiment of the present invention.
FIG. 12C is a front view of one embodiment of the present invention.
FIG. 12D is a cut-through view of one embodiment of the present invention.
FIG. 12E is a cut-through view of one embodiment of the present invention.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The current invention addresses numerous issues with the prior art and includes access to the stone in addition to providing a means for the removal of the stone fragments through negative pressure suction. Referring to the figures, where like numerals refer to like elements, there is shown a device for removing a stone, a stone fragment, or a foreign body from a patient comprising a suction evacuation assembly 5 which includes a primary sheath 10 which has a proximal end 11, a distal end 12 and an outer surface 14 wherein the distal end 12 is a flexible, deflectable tip 15, allowing it to be actively or passively deflected, an obturator 60 which is inserted into the proximal end 11 of the primary sheath 10 and which extends beyond the distal end 12 of the sheath 10 and is releaseably secured to the sheath 10, a side arm 30 emanating from the outer surface 14 of the primary sheath 10, a deflection mechanism 98 secured to the primary sheath 10 which is operationally associated with the deflectable tip 15 which will enable the user to adjust the direction of the distal end 12 of the primary sheath 10 to aid with the direction of suction, irrigation, instrument placement, or removal of a stone, stone fragment or any other foreign body or tissue from a patient and a secondary sheath 70 which has a proximal end 71, a distal end 72 and an outer surface 74, designed to be inserted into the primary sheath 10, the secondary sheath 70 has a dual lumen 83, 93 with an oblong shape wherein the dual lumen allow passage of surgical instruments and irrigation fluid and wherein the oblong shape provides for adequate space for the egress of stone fragments and fluid through the lumen of the primary 13 and/or secondary sheath 73, wherein the distal end 72 is flexible, allowing it to be actively or passively deflected and wherein the secondary sheath 70 is longer than the primary sheath 10 allowing the distal end 72 of the secondary sheath 70 to extend beyond the distal end 12 of the primary sheath 10 in order to allow irrigation, a catheter, a foreign body basket, a backstop, an instrument or device to be passed to or beyond a stone, a stone fragment or other foreign body during a procedure to remove them; and wherein the obturator 60 is withdrawn from the primary sheath 10 and the secondary sheath 70 is inserted into the primary sheath 10 and into the patient in order to facilitate the removal of the stone, stone fragment or foreign body.

Sheath, as used herein, refers to a rigid, semi-rigid, or flexible tube. The primary sheath 10 can be constructed from any medical grade material including, but not limited to, nylon, polyethylene, polyvinyl chloride, polycarbonate, polypropylene, or fluorinated ethylene propylene. The primary sheath 10 may be reinforced with a rigid or a semi-rigid coil or filaments within its wall to add additional rigidity if desired. In one embodiment of the present invention, the primary sheath 10 is reinforced with radiopaque material. In another embodiment of the present invention, the primary sheath 10 may further include one or more radiopaque materials. The primary sheath 10 has a proximal end 11 through which instruments may be inserted and withdrawn. The primary sheath 10 has a distal end 12 which is inserted into a patient. The primary sheath 10 also has a lumen 13 and an outer surface 14. The length of the primary sheath 10 may correspond to any length known in the art. In one embodiment, the length of the primary sheath is in the range of 15 to 65 cm. The lumen 13 of the primary sheath may be any diameter permits the passage of a scope which is commonly used in Lithotripsy. In one embodiment, the lumen may have a diameter in the range of 2.5 to 8 mm or 8 to 24 French. The primary sheath 10 may include markings on the outer surface 14 of the primary sheath which may aid in determining the position of the primary sheath within a patient based on distance. A radio-opaque material may also be used on the outer surface 14 of the primary sheath to aid in determining the position of the primary sheath within a patient.

A primary sheath 10 further includes a handle chamber 20 located at the proximal end 11 of the primary sheath or the proximal end 41 of a proximal sheath 40. FIGS. 1-6 and 8-14 contain numerous embodiments of a handle chamber 20. A handle chamber 20 includes a proximal end 21, a distal end 22, a lumen 23, in outer surface 24, and arresting wall 25 and a color band 26 which is located on the outer surface. A handle chamber 20 is designed to be operationally associated with a secondary sheath 70 which is described below.

In one embodiment of the present invention, the distal end 12 of the primary sheath 10 is made of expandable material or expansion mechanism 17. Once the distal end 12 is inserted into a patient's body cavity or lumen it can be expanded by an expansion balloon, an expansion spring, or some another mechanism. The expanded distal end 12 can then be used to entrap the stone, foreign body, tissue or targeted organ inside the sheath for treatment. The expanded distal end 12 can also be used to simply anchor the primary sheath 10 in a desired position. In yet another embodiment, the distal end 12 of primary sheath 10 is constructed in a tapered configuration to facilitate the insertion of the primary sheath into the patient's body cavity and lumen. Once the distal end 12 of primary sheath 10 is in place, the distal end 12 can then be expanded as needed. In another embodiment, a suction evacuation assembly 5 further comprises an expansion mechanism 17 located within the lumen 13 of the primary sheath 10 or on the obturator 60 and an expandable, flexible distal end 12 is operationally associated with the expansion mechanism 17, wherein the distal end 12 of the primary sheath 10 or a distal sheath 50 is introduced into a smaller cross section and located into a desired position or orientation at which time the expansion mechanism 17 is activated and expanded which expands the flexible distal end 12, 52 of the sheath, creating a larger cross section through internal expansion. In still another embodiment, the distal end 12, 52 of a primary sheath 10 or a distal sheath 50 may be collapsible or foldable (e.g. accordion-like or fold up like an umbrella) prior to expansion when then unfolds, expands and/or extends as an expansion mechanism 17 is activated to increase the diameter/cross-section of the sheath.

In one embodiment of the present invention the primary sheath 10 is comprised of a proximal sheath 40 and a distal sheath 50 in respect to the operator holding the device. The two sheaths (i.e., a proximal sheath 40 and a distal sheath 50) can be joined together as a single piece or can be joined together in a sleeve type connection.

The proximal sheath 40 has a proximal end 41 and a distal end 42. The proximal sheath 40 also includes a lumen 43 through which tools, instruments, stones and foreign bodies pass and an outer surface 44. The proximal sheath 40 is transparent or semi-transparent so that the stone fragments can be visualized as they travel up the lumen 43 and exit the side arm 30. The proximal sheath 40 has a connection fitting to receive a flexible cap 68. One embodiment of the present invention uses a hat like connecting joint. The proximal sheath 40 also has a connection mechanism 45 that allows for a secure connection between the proximal sheath 40 and the obturator 60. This connection will prevent separation of obturator 60 from the proximal sheath 40 during the insertion into a patient's body luminal cavity. This connection can be constructed in various shapes or types and includes a simple male to female screw-on connection. In one embodiment of the present invention, the female end of the connection is on the proximal end 41 of the proximal sheath 40. In one embodiment, the length of the proximal sheath 40 may be in the range of 4 to 8 cm. The outer surface 44 of the proximal sheath 40 has one or more side arms 30.

The distal sheath 50 has a proximal end 51 and a distal end 52. The distal sheath 50 also includes a lumen 53 through which tools, instruments, stones and foreign bodies pass, an outer surface 54 and a lock 55 which is used to connect the proximal sheath 40 and the distal sheath 50 together and maintain the connection for as long as desired. Alternatively, the distal sheath 50 and the proximal sheath 40 can be constructed as a single piece in a straight or in arm over sleeve type configuration. The distal sheath can be straight, tapered, expandable, or flared. The distal end 52 of the distal sheath 50 can be flat, beveled, convex, or concave. The preferred embodiment is a straight distal sheath 50 with a flat end. The distal end 52 may be coated with hydrophilic coating and/or polytetrafluoroethylene to reduce friction especially in a fluid environment. The distal sheath 50 can be opaque, semi-transparent, transparent, or a combination of these. In the preferred embodiment, the distal sheath 50 is opaque to avoid reflection of illuminating light of endoscope. The distal sheath 50 may also have measurement markings to indicate the length of distal sheath has been advanced into the body cavity. The length of the distal sheath 50 may be in the range of 15 to 45 cm.

In one embodiment of the present invention, the distal end 12, 52 of the primary sheath 10 and/or distal sheath 50 includes a deflectable tip 15 which will enable the user to adjust the direction of suction, irrigation, instrument placement, or removal of a stone, stone fragment or any other foreign body or tissue from a patient. The deflectable tip 15 has a length in the range of 4 to 10 cm. The deflectable tip 15 is deflectable to any angle desired by the user of the device. The deflectable tip 15 may have memory which is to say that the deflectable tip 15 may be configured into a specific angle or form and retain that configuration. It can be inserted into the body in another configuration, i.e., straight, until it is manipulated into a specific location by the user of the device. The deflectable tip 15 can then be reverted back to the original shape. The distal portion 12, 52 of the primary sheath 10 and/or distal sheath 50 can also be deflected either actively or passively. In the active mold, the distal sheath is straight. A cable or some other mechanism along the inner (lesser) curvature of the bend can be either withdrawn or shortened gradually thus bending the distal portion 12, 52 of the primary sheath 10 and/or distal sheath 50 to a maximum of 360 degrees. In the passive mold, the distal portion 12, 52 of the primary sheath 10 and/or distal sheath 50 has an inherent bend of up to 360 degrees. The bendable portion can either be gradually straightened by withdrawing or shortening a cable or some other mechanism along the outer (greater) curvature of the bend or by using the rigid/semi-rigid obturator. In the preferred embodiment the bending section is about 4-6 cm. The flexible distal end 12, 52 is deflected by active mode. In another embodiment the distal end 12, 52 of the primary sheath 10 and/or distal sheath 50 has a balloon that can be inflated to hold the sheath in place within the body cavity. In still another embodiment, a balloon assembly, or other anchoring mechanism known in the art, is operationally associated with the distal end 12, 52 of the primary sheath 10 and/or distal sheath 50. When the suction evacuation assembly 5 is inserted into a patient and placed in a desired location, the balloon is inflated to hold the primary sheath 10 in place. This is especially useful when it is placed within the lumen or cavity of a patient's body.

In one embodiment of the present invention the proximal 40 and distal sheath 50 can be separated from one another. The distal sheath 50 is constructed with a peelable (tearable) material. This can also be achieved with a fabricated perforation along the longitudinal axis of the distal sheath 50. In a preferred embodiment, there are two lateral wings placed at the proximal ends of the distal sheath 50. This will facilitate the separation (peeling, tearing). In another embodiment the distal sheath 50 can be expanded. This can be achieved with an expansion balloon, an expansion spring, or some other mechanical means. The expansion can achieve two effects:

(1) Dilate the space where the distal sheath 50 traverses, and (2) Entrap the target within the distal sheath 50 for fragmentation, morcellation, ablation, or extraction.

The side arm 30 emanates up from the outer surface 14 of a primary sheath 10 or the outer surface 44 of a proximal sheath 40 and forms an angle with the sheath 10, 40 in the range of >0° to <180°, between 10° and 170°, between 20° and 160°, between 30° and 150°, between 20° and 110°, between 20° and 90°, or between 20° and 70°. In one embodiment, the angle is 45° toward the proximal end 11, 41 of the sheath 10, 40. In another embodiment, the angle is 30° toward the proximal end 11, 41 of the sheath 10, 40. In still another embodiment, the angle is 25° toward the proximal end 11, 41 of the proximal sheath 10, 40. In one embodiment, the diameter of the lumen 33 of the side arm 30 is up to 20% smaller than the diameter of the lumen 13, 43, 53 of a primary sheath 10, a proximal sheath 40 and a distal sheath 50. In another embodiment, the diameter of the lumen 33 of the side arm 30 has a diameter which is the same or up to 20% larger than the diameter of the lumen 13, 43, 53 of a primary sheath 10, a proximal sheath 40 and a distal sheath 50. In yet another embodiment, the diameter of the lumen 33 of the side arm 30 is the same or larger than the diameter of the lumen of the sheath 13, 43, 53 to facilitate the efficient evacuation of stones, stone fragments or other foreign bodies. Each side arm 30 includes a proximal end 31 and a distal end 32 with the distal end 32 being secured to the outer surface 14, 44 of a primary sheath 10 and/or a proximal sheath 40. The side arm 30 may also include a pressure regulating mechanism 110. The pressure regulating mechanism 110 may simply be a control vent in the form of a slit or a hole, or it may be a more elaborate mechanism such as a valve. In one embodiment of the present invention, a side arm 50 has a pressure regulating mechanism 37 in the form of a longitudinal slit in respect to the axis of the side arm 30 and acts as a control vent. When minimum negative pressure is required, the slit is left open or minimally occluded. When more negative pressure is required the slit is further occluded as needed to a maximum of complete closure. In another embodiment the pressure regulating mechanism 37 is placed on the egress tubing (connecting to the negative pressure system 150) in the form of a three-way valve. Additionally, the egress tubing has two perpendicular sluices; the second sluice can be used to clear blood clots, tissue fragments, or stone fragments that might have been aspirated into the egress tubing and cause blockage. In another embodiment, a rubber or silicone seal is attached to the side arm 30. This seal can be used to close the control vent and relieve the operator from the burden of manually closing the control vent. In yet another embodiment, a push-pull mechanism is employed to close and open the control vent instead of having the operator manually close the control vent. Furthermore, the pressure regulating mechanism 37 can be placed anywhere along the egress path (i.e. the side arm 30, the connecting tubing 130, the collection container 140 or even on the aspirator (negative pressure system)).

The proximal end 31 of the side arm 30 is configured to accept a connection to a flexible tubing 130. The proximal end 31 can be straight, flared, tapered, expandable, and/or ribbed and/or have a luer lock or some other type connector which may be used in conjunction with a variety of medical instruments known in the art which include, but are not limited to, a wire basket retriever, a guide wire, a stylet, a loop, a grasper, a needle, or the like. A backflow preventer may also be associated with the proximal end 31 of the accessory side arm. In one embodiment, the proximal end 31 is straight to avoid compromising the lumen 33 of the side arm 30 and thus reduce the efficiency of stone removal. In another embodiment, a marking is placed just proximal to the connection of the side arm 30 and the outer surface 14, 44 of a primary sheath 10 and/or proximal sheath 40. This marking can be seen both endoscopically and/or externally. The marking may be any color or material which may be easily visualized by the user of the suction evacuation assembly 5. In one embodiment, the side arm 30 further comprises a pressure regulating mechanism 37 which allows a person using the suction evacuation assembly 5 and to increase or decrease the negative pressure within the suction evacuation assembly.

The instant invention further includes a secondary sheath 70 which has a proximal end 71, a distal end 72, a lumen 73, an outer surface 74. The secondary sheath 70 can be constructed from any medical grade material including, but not limited to, nylon, polyethylene, polyvinyl chloride, polycarbonate, polypropylene, or fluorinated ethylene propylene. The secondary sheath 70 may be reinforced with a rigid or a semi-rigid coil or filaments within its wall to add additional rigidity if desired. In one embodiment of the present invention, the secondary sheath 70 is reinforced with radiopaque material. In another embodiment of the present invention, the secondary sheath 70 may further include one or more radiopaque materials. The secondary sheath 70 has a dual lumen with an oblong shape wherein the dual lumen allows passage of surgical instruments and irrigation fluid and wherein the oblong shape provides for adequate space for the egress of stone fragments and fluid through the primary sheath 10 and/or the secondary sheath 70. Looking to FIGS. 1, 2, 6, 7 and 10-13, several embodiments of a secondary sheath 70 are illustrated. A secondary sheath 70 may further include a deflectable tip 75. The deflectable tip 75 is operationally associated with the deflectable tip 15 of a primary sheath 10 and/or a distal sheath 50. The deflectable tip 75 is operationally associated with the deflection mechanism 98 and its inner working element. The deflectable tip 75 functions in a manner identical to or similar to the deflectable tip 15 described above. A secondary sheath 70 further includes a primary barrel 80, a secondary barrel 90 and a bridge 88 which joins the primary barrel 80 to the secondary barrel. A primary barrel 80 has a proximal end 81, a distal end 82, a lumen 83 and an outer surface 84. A secondary barrel 90 has a proximal end 91, a distal end 92, a lumen 93 and an outer surface 94. A primary barrel 80 may further include a connector 86 located at its proximal end 81 and a secondary barrel may further include a connector 96 located its proximal end 91. Each connector 86, 96 may be used to secure a flexible cap, a sealing cap, a tube or an instrument to the proximal end of either barrel. In one embodiment of the present invention, the bridge 88 joins the first barrel 80 and the second barrel 90 together along the entire length of each barrel. In another embodiment, the bridge 88 runs between the first barrel 80 and the second barrel 90 from the distal ends of each barrel (82 and 92 respectively) to just short of the proximal ends of each barrel (81 and 91 respectively). In one embodiment of the instant invention, the proximal ends of each barrel (81 and 91 respectively) extend between 2 and 20 cm, between 4 and 15 cm or between 5 and 10 cm beyond the distal end 79 of the stabilizing/insertion handle. In another embodiment, the proximal ends of each barrel (81 and 91 respectively) are flexible, poseable (i.e. they retain their shape when posed in a particular configuration), rigid or a combination thereof.

The length of the secondary sheath 70 may correspond to any length known in the art. In one embodiment, the length of the primary sheath is in the range of 15 to 75 cm. The total lumen 73 (83+93) of the secondary sheath may be any diameter permits the passage of a scope which is commonly used in Lithotripsy. In one embodiment, the lumen may have a diameter in the range of 2.5 to 8 mm or 8 to 24 French. The secondary sheath 70 may include markings on the outer surface 74 of the secondary sheath which may aid in determining the position of the secondary sheath within a patient based on distance. A radio-opaque material may also be used on the outer surface 74 of the secondary sheath to aid in determining the position of the secondary sheath within a patient. In a preferred embodiment the length of a secondary sheath 70 is approximately 3 to 10 cm longer, 3 to 8 cm longer or 3 to 5 cm longer than the length of a primary sheath 10.

A secondary sheath 70 also includes a stabilizing/insertion handle 77 which may be used to handle, manipulate and control the secondary sheath 70. The stabilizing/insertion handle 77 includes a proximal end 78 and a distal end 79. In one embodiment of the instant invention, the stabilizing/insertion handle 77 is between 2.5 and 5 cm in length. The stabilizing/insertion handle 77 aids to stabilize the secondary sheath 70 when it is engaged to the primary sheath 10. In its use, a suction evacuation assembly 5 includes an obturator 60 which is inserted into the lumen 13 of primary sheath 10. The distal end 12 of the primary sheath is then inserted into a patient and the obturator 60 is withdrawn from the primary sheath 10. A secondary sheath 70 is then inserted into the lumen 13 of the primary sheath. This may be accomplished by the user holding the stabilizing/insertion handle 77 while the secondary sheath 70 is inserted into the primary sheath 10. The handle chamber 20 which is located on the primary sheath 10 is designed to engage and be operationally associated with the stabilizing/insertion handle 77. When the secondary sheath 70 is fully inserted into the primary sheath 10 the distal end 79 of the stabilizing/insertion handle engages with the arresting wall 25 of the handle chamber (FIG. 2) and prevents the secondary sheath 70 from traveling further within the primary sheath 10, thus occludes the egress channel 33 of the side arm 30. Simultaneously the secondary sheath is designed so that its distal end 72 will extend beyond the end of the distal end 12 of the primary sheath and the proximal ends 81, 91 of the primary barrel 80 and secondary barrel 90 remain free to be manipulated as necessary.

A suction evacuation assembly 5 further includes a deflection mechanism 98 secured to the outer surface primary sheath 10 which is operationally associated with the flexible, distal ends 12, 52, 72 of the primary sheath 10, the distal sheath 50\and the secondary sheath 70 which will enable the user to adjust the direction of the distal ends of the sheaths to aid with the direction of suction, irrigation, instrument placement, or removal of a stone, stone fragment or any other foreign body or tissue from a patient. A key component of the instant invention is the fact that the distal end of the primary 10, distal 50 and secondary 70 sheath is flexible, allowing it to be actively or passively deflected and wherein the secondary sheath 70 is longer than the primary sheath 10 allowing the distal end 72 of the secondary sheath to extend beyond the distal end 12 of the primary sheath in order to allow irrigation, a catheter, a foreign body basket, a backstop, an instrument or device to be passed to or beyond a stone, a stone fragment or other foreign body during a procedure to remove them from a patient.

Obturator 60, as used herein, refers to an instrument which is known in the laparoscopic art. The obturator 60 is made of rigid, semi-rigid, or flexible material and may have a shaft 65 with an outer surface 64 which is either roughened or smooth in texture. An obturator 60 may have a solid center or a hollow center including a lumen 63. The obturator 60 has a proximal end 61 and a distal end 62 which is inserted into the lumen 13 of primary sheath 10. The distal end 62 may be straight, round, tapered, or beveled. The obturator 60 is to fit snuggly in the primary sheath 10. In one embodiment of the present invention, the obturator 60 has a hollow center creating a lumen 63 and a tapered distal end 62 and a guide wire may be passed through the lumen 63. In another embodiment, the obturator 60 is solid and the distal end 62 is beveled. The proximal end 61 of the obturator may be constructed as a handle for easy grasping and with a luer lock mechanism to allow for the attachment of an injection syringe. One embodiment may include a connection mechanism at distal end 62 of the obturator located at the interface between the obturator and the proximal end 11 of the primary sheath 10. In another embodiment the obturator 60 includes a male to female type screw on connector which allows the obturator 60 to be engaged to the proximal end of the primary sheath 10 after insertion into the primary sheath. The screw on connector may also be disengaged later and the obturator 60 withdrawn from the lumen 13 of the primary sheath. In still another embodiment the connection is made by twisting of a luer lock mechanism on the obturator and the primary sheath. This will prevent the disengagement of the primary sheath 10 from the obturator 60 during the passage of the primary sheath 10 through the body. In one embodiment of the instant invention, an obturator 60 further includes, a central lumen 63 which may accommodate a tool such as a guide wire or needle, and an expandable portion 67 of the distal end 62 of the obturator, such as a balloon that can be inflated to hold the obturator 60 in place within a patient, or an anchoring mechanism operationally associated with the distal end 62 of the obturator.

Flexible cap, as used herein, refers to a device which is constructed to fit the proximal end 11 of the primary sheath 10. The center opening may be self-sealing and the cap may be comprised of rubber, silicone, or any material known to be acceptable in the art.

Connecting tubing 130 is well known in the art. Connecting tubing 130 can be rigid, semi-rigid, or flexible tube of any medical grade material. Each piece of tubing as a proximal end 131 and a distal end 132, a lumen 133 through which material may travel and an outer surface. In one embodiment, the tubing is made of a clear PVC tubing. The tubing is used to connect a side arm 30, or any part thereof to either a collection container 140, a negative pressure system 150, or any other device known in the art. In one embodiment of the present invention, a primary tube 136 is connected by one end to a side arm 30 and connected at the opposite end to an ingress opening 142 on a collection container 140 and a secondary tube 138 is connected by one end to an egress opening 143 on a collection container 140 and connected at the opposite end to a negative pressure system 150.

Figure 13:
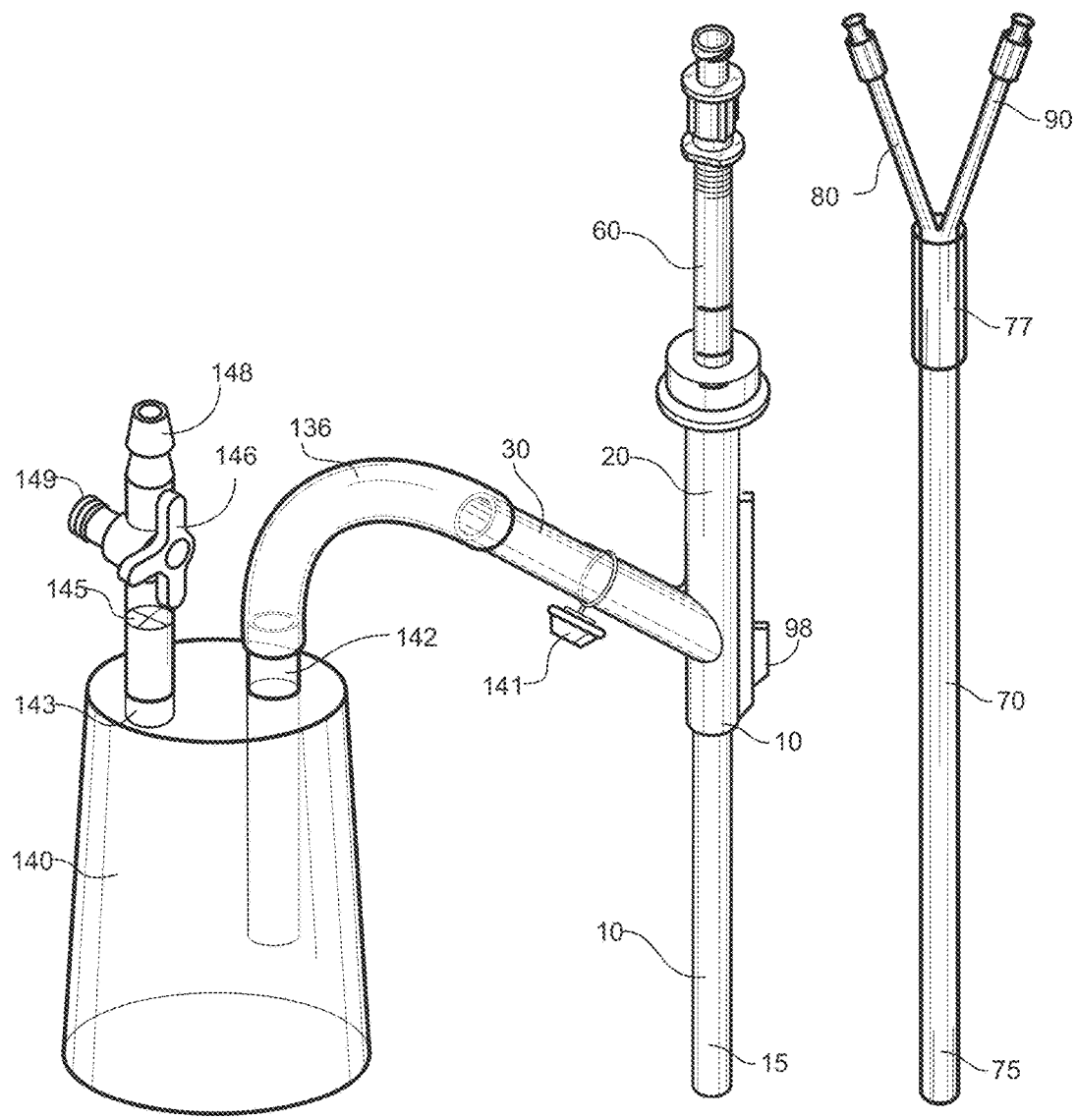
FIG. 13 is a perspective view of one embodiment of the present invention.
Figure 14:
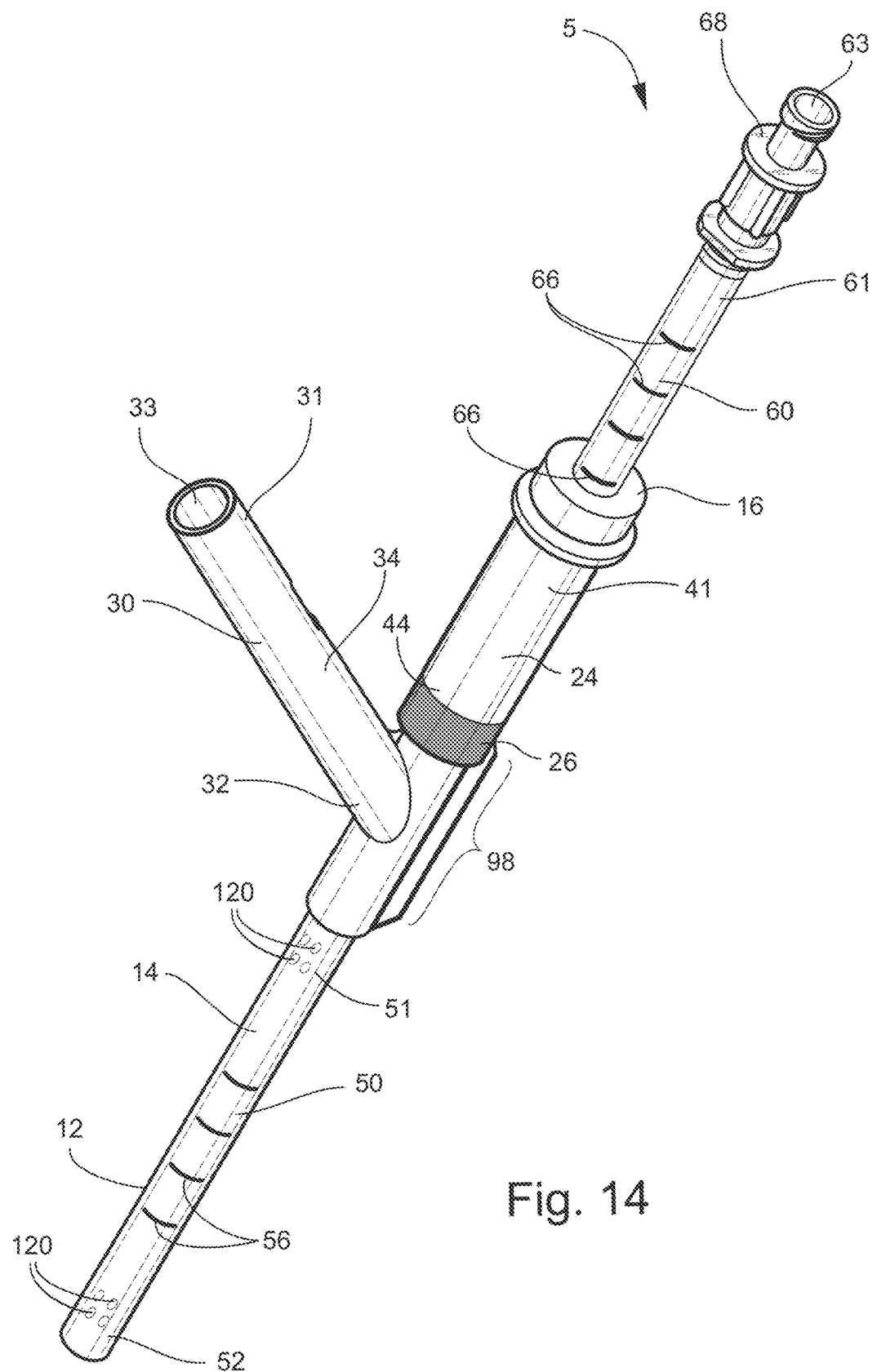
FIG. 14 is a perspective view of one embodiment of the present invention.
Figure 15A:
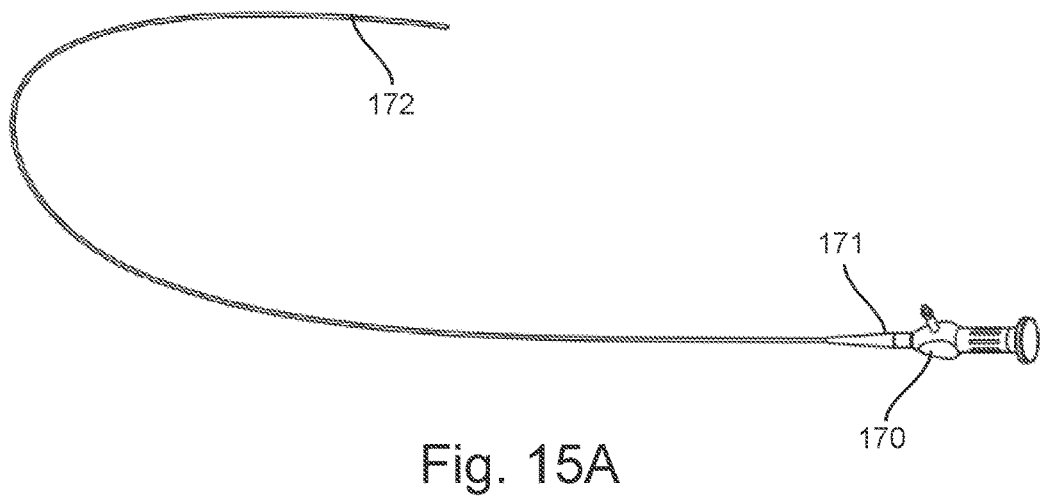
FIG. 15A is perspective view of an embodiment of a scope used in the present invention.
Figure 15B:
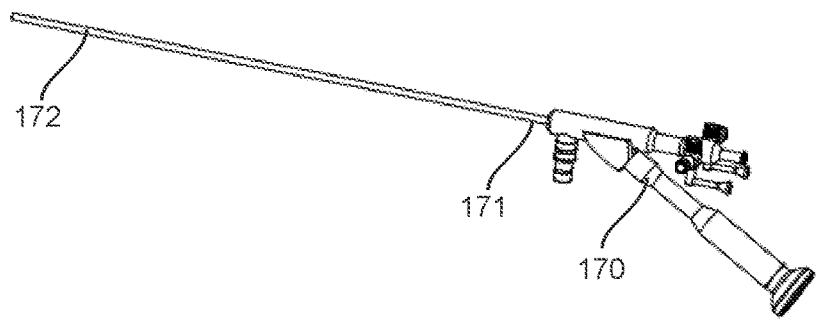
FIG. 15BA is perspective view of an embodiment of a scope used in the present invention.
Figure 15C:
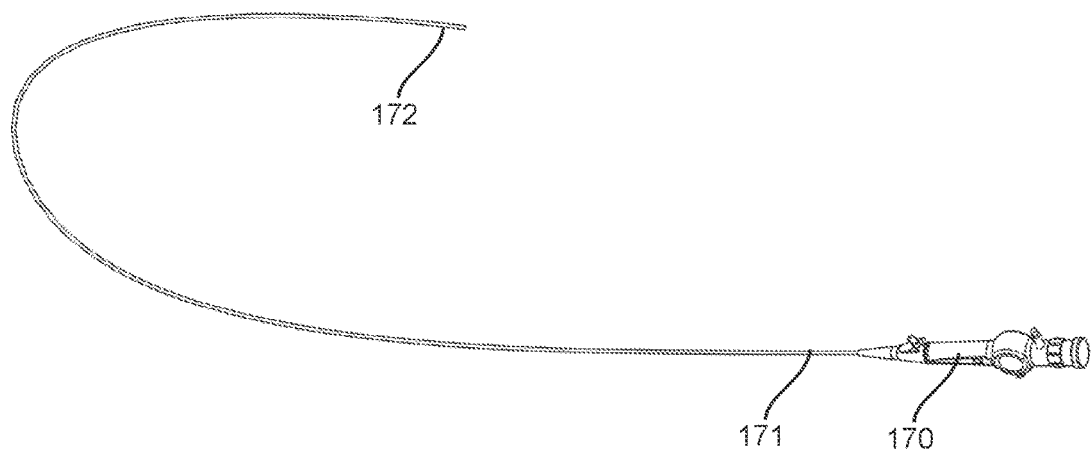
FIG. 15C is perspective view of an embodiment of a scope used in the present invention.
Figures 16A, 16B:
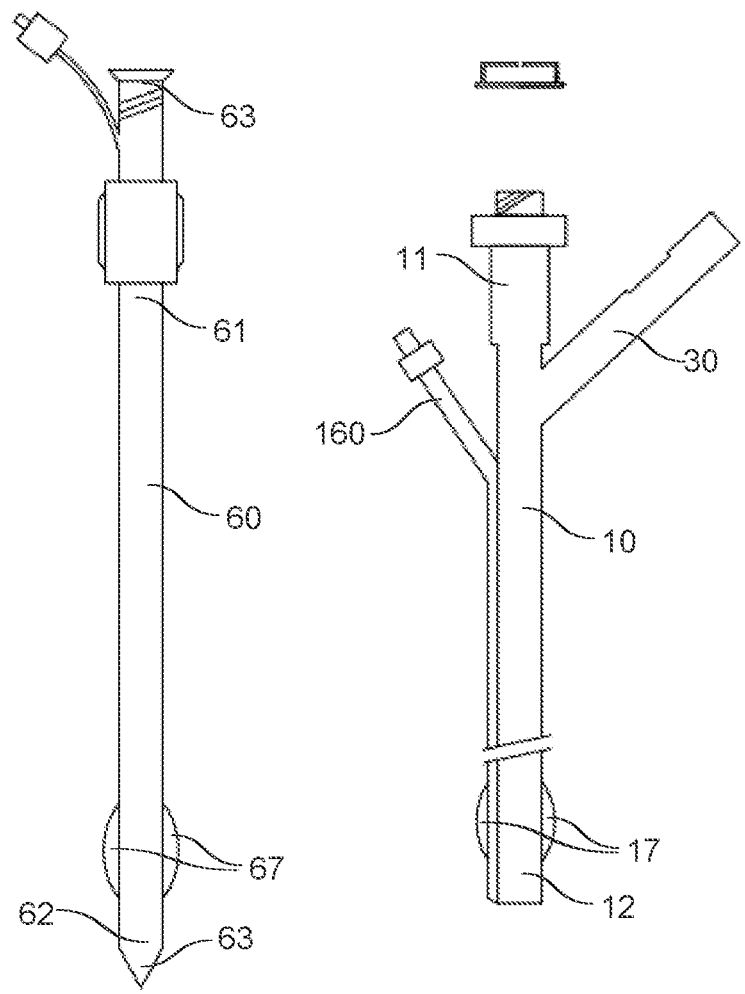
FIG. 16A is a front view of one embodiment of the present invention.
FIG. 16B is a front view of one embodiment of the present invention.

Collection container 140 is a container of any shape. It has a cap 141 and a bottom. The cap has an ingress (intake) opening 142 into and an egress (outflow) opening 143. The ingress opening 142 may or may not have a one-way valve to prevent regurgitation of fluid and other materials into the connecting tubing 130. The egress opening 143 or anywhere along the egress tubing may be fitted with a sieve like mechanism to prevent the outflow of small stone or foreign body fragments or other materials from the collection container 140. The ingress opening has a connecting mechanism for connection to the connecting tubing 130. The egress channel has connecting mechanism to connect to a standard negative pressure aspiration machine. The bottom of the collection container 140 may contain a screw on or pull tab mechanism for the removal of specimen from the collection container 140. In one embodiment, the ingress tubing 142 is a longer, rigid tube which extends deeper into the collection container 80 while the egress tubing 143 is a shorter, rigid tube with a sieve 145 at the end that is inside the collection container. The bottom of the collection container has a pull tab for removal of collected specimens. In another embodiment, the egress tubing 143 is fitted with a side arm having a three-way valve 146 (FIG. 13). The straight arm 148 is connected to the negative pressure system 150 while the right angle arm 149 is connected to a syringe. In normal operation the right angle side arm is closed. However, when there are stone fragments, blood clots, or tissue fragments obstructing the egress tubing 143, the right angle port can be opened to clear the obstructing objects by using irrigation with the attached syringe.

In one embodiment of the instant invention, a proximal end of a primary tube 136 is releaseably secured to the side arm 30 and a distal end of the primary tube releaseably secured to a collection container 140 and a proximal end of a secondary tube 138 is releaseably secured to the collection container 140 and a distal end of the secondary tube is releaseably secured to a negative pressure system 150 wherein the negative pressure system is activated in order to remove the stone or foreign body from the cavity if a diameter of the stone or foreign body is narrower than an inside diameter of the lumen of the sheath and the side arm 30, or lithotripsy is performed on the stone or the foreign body in order to create fragments with a decreased diameter which allow the passage of the fragments within the inside diameter of the primary 13 and/or secondary 73, 83, 93 sheath and the side arm 33 and the stone, foreign body and/or fragments are collected in the collection container 140.

In still another embodiment, the suction evacuation assembly 5 may further include a needle assembly (not illustrated). A blunt or sharp tip needle which is longer than the obturator 60, which can be passed through the lumen 63 of the obturator and is releaseably secured to the obturator 60. The needle assembly includes a needle sheath with an inner channel and an outer surface and needle shaft (i.e., a solid puncturing shaft with a solid core or a hollow shaft) which are releaseably secured to one another with a locking mechanism (i.e. a luer lock). The needle shaft is inserted into the sheath forming the needle assembly which is inserted into an obturator 60 which is then inserted into the lumen 13 of a primary sheath 10. The entire assembly is then inserted into a patient. The needle shaft may be any needle known in the art with sufficient length to allow the tip of the needle shaft (i.e. the distal end) to extend 1 to 5 cm (preferably 1-3 cm) beyond the distal end 12 of the primary sheath 10 while control of the proximal end of the needle shaft is maintained at the proximal end 11 of the primary sheath. In one embodiment of the instant invention, the needle shaft is echogenic so that it can be identified and located by ultrasonography. The tip of the needle shaft may be selected from the group comprising a blunt tip needle, a bevel tip needle, a Salinger (3 facets cutting) tip, or any other tip known in the art. The inner channel of the needle sheath has an inside diameter that can accommodate a standard guide-wire. In one embodiment, the entire suction evacuation assembly 5 as described above can be inserted into a patient in a single step maneuver without dilation. In another embodiment, the entire suction evacuation assembly 5 as described above can be inserted when a guide-wire has been placed through the inner channel of the needle sheath, after removing the needle shaft, and positioned in a desired location (i.e. a kidney). The fully assembled needle assembly, obturator 60 and primary sheath 10 can then be inserted in a single step without stepwise dilation of the surrounding tissue.

One embodiment of the instant invention further includes a scope which has a diameter that is smaller than the inner diameter of the lumen 13 of the primary sheath or either lumen of the secondary sheath 73, 83, 93 resulting in an open channel within at least one lumen of the primary sheath 10 or secondary sheath 70 which permits the passage of stones, pieces of stones or other foreign objects through the lumen 13, 73, 83, 93 or through the lumen of the primary sheath 13 and through the lumen of the side arm 33.

In one embodiment of the instant invention, the suction evacuation assembly 5 further comprises a guide wire (not illustrated) which is introduced into a lumen or cavity of a patient's body containing one or more stones or foreign bodies prior to inserting the primary sheath 10 into the lumen or cavity of a patient's body in order to aid in the positioning the distal end of the obturator 62, primary sheath 12 and/or secondary sheath 72 in a position in close proximity to the stones or foreign bodies and the secondary sheath 70 may be used to guide additional irrigation, a catheter, a foreign body basket, a backstop, an instrument or device to the position in close proximity to the stones or foreign bodies simultaneously with the scope and/or irrigation, catheter, foreign body basket, backstop, instrument or device through the primary sheath 10.

In another embodiment, the section evacuation assembly 5 further includes one or more holes 120 (FIG. 14) located on the primary sheath 10 wherein the holes extend from the outer surface 14 of the primary sheath 10 through to the lumen 13 of the primary sheath and allow for the draining/evacuation of urine or any other fluid from a patient during a procedure without requiring the removal of the obturator or the secondary sheath. The holes 120 may be located near the handle of the primary sheath 10 or at the distal end 12 of the primary sheath. In one preferred embodiment, the distal end of the primary sheath 10 may be located within or near the bladder and the holes 120 are used to aid in draining urine out of a patient's bladder. In still another embodiment the section evacuation assembly 5 further includes an accessory channel 160 secured to the outer surface 14 of the primary sheath 10, the accessory channel 160 includes a proximal end 161 with a connector 164 and a distal end 162 located in the proximity of the distal end 12 of the primary sheath 10 and a lumen 163 running within the entire length of the accessory channel 160.

The present invention further involves a method of using a suction evacuation assembly 5 for removing one or more stones or foreign bodies from within a patient comprising the steps of:

a) providing a suction evacuation assembly 5 which includes:

a primary sheath 10 which has a proximal end 11, a distal end 12, a lumen 13 and an outer surface 14 wherein the distal end 12 is flexible, allowing it to be actively or passively deflected;

an obturator 60 which is inserted into the proximal end 11 of the primary sheath 10 and which extends beyond the distal end 12 of the sheath and is releaseably secured to the sheath;

a side arm 30 emanating from the outer surface 14 of the primary sheath 10;

a deflection mechanism 98 secured to the primary sheath 10 which is operationally associated with the flexible, distal end (deflectable tip 15) which will enable the user to adjust the direction of the distal end 12 of the sheath to aid with the direction of suction, irrigation, instrument placement, or removal of a stone, stone fragment or any other foreign body or tissue from a patient; and a secondary sheath 70 which has a proximal end 71, a distal end 72 a lumen 73, and an outer surface 74, wherein the secondary sheath 70 is designed to be inserted into the primary sheath 10, the secondary sheath has a dual lumen 83, 93 with an oblong shape wherein the dual lumen allows passage of surgical instruments and irrigation fluid and wherein the oblong shape provides for adequate space for the egress of stone fragments and fluid through the primary 10 and/or secondary sheath 70;

wherein the distal end 72 is flexible, allowing it to be actively or passively deflected and wherein the secondary sheath 70 is longer than the primary sheath 10 allowing the distal end 72 of the secondary sheath to extend beyond the distal end 12 of the primary sheath in order to allow irrigation, a catheter, a foreign body basket, a backstop, an instrument or device to be passed to or beyond a stone, a stone fragment or other foreign body during a procedure to remove them;

b) inserting an obturator 60 into the proximal end 11 of the primary sheath 10 which extends beyond the distal end 12 of the primary sheath and releaseably securing the obturator 60 to the primary sheath 10;

c) inserting the distal end 12 of the primary sheath and obturator 60 into a patient's body containing one or more stones or foreign bodies;

d) positioning the distal ends 12, 62 of the primary sheath and the obturator in a position in close proximity to the stones or foreign bodies;

e) disengaging the obturator 60 from the proximal end 11 of the primary sheath and removing the obturator 60 from the primary sheath 10;

f) inserting the secondary sheath 70 into the proximal end 11 of the primary sheath and extending the distal end 72 of the secondary sheath beyond the distal end 12 of the primary sheath and releaseably securing the secondary sheath 70 to the primary sheath 10;

g) connecting one end of a primary tube 136 to the side arm 30 and connecting the other end of the primary tube to a collection container 140;

h) connecting one end of a secondary tube 138 to the collection container 140 and connecting the other end of the secondary tube to a negative pressure system 150;

i) inserting a scope into either the primary sheath 10 or the secondary sheath 70 and into the patient;

j) adjusting the direction of the deflectable tip 15 of the distal end 12, 72 of the primary and secondary sheaths using the deflection mechanism 98;

k) visualizing the stone or foreign body using the scope;

l) activating the negative pressure system 150 in order to remove the stone or foreign body from the cavity if a diameter of the stone or foreign body is narrower than an inside diameter of the lumen of the sheath and the side arm, or m) performing a lithotripsy on the stone or the foreign body in order to create fragments with a decreased diameter which allow the passage of the fragments within the inside diameter of the lumen of the sheath and the side arm or in the space between the primary and secondary sheath and the side arm; and n) Withdraw secondary sheath to just distal to the side arm 30 to allow egress of stone, foreign body, or tissue fragments when such fragments are too large for the space between primary sheath 10 and secondary sheath 70.

o) collecting the stone, foreign body and/or fragments in the collection container 140.

In one embodiment of the above method, the secondary sheath 70 further includes a stabilizing/insertion 77 handle which aids with insertion of the secondary sheath 70 within the primary sheath 10 and aids to stabilize the secondary sheath 70 when it is engaged to the primary sheath 10. More specifically, the primary sheath 10 further includes a handle chamber 20 located at the proximal end 11 of the primary sheath or the proximal end 41 of a proximal sheath 40. FIGS. 1-6 and 8-14 contain numerous embodiments of a handle chamber 20. A handle chamber 20 includes a proximal end 21, a distal end 22, a lumen 23, in outer surface 24, and arresting wall 25 and a color band 26 which is located on the outer surface. The handle chamber 20 is designed to engage and be operationally associated with the stabilizing/insertion handle 77. When the secondary sheath 70 is fully inserted into the primary sheath 10 the distal end 79 of the stabilizing/insertion handle engages with the arresting wall 25 of the handle chamber (FIG. 2) and prevents the secondary sheath 70 from traveling further within the primary sheath 10 thus occluded the lumen 34 of side arm 30. Simultaneously the secondary sheath is designed so that its distal end 72 will extend beyond the end of the distal end 12 of the primary sheath and the proximal ends 81, 91 of the primary barrel 80 and secondary barrel 90 remain free to be manipulated as necessary.

In another embodiment of the above method, the primary sheath 10 is comprised of a proximal sheath 40 and a distal sheath 50 wherein the distal sheath 50 is separable from the proximal sheath 40 and the proximal sheath is the same size or larger than the distal sheath. In yet another embodiment, a distal sheath 50 or the distal portion 12 of a primary sheath 10 is made of a releasable, peelable material which may be peeled off of the distal sheath 50 or the distal portion 12 of a primary sheath 10 when no longer needed or wanted.

The above method may further comprise the step of introducing a guide wire into a lumen or cavity of a patient's body containing one or more stones or foreign bodies prior to inserting the primary sheath 10 into a lumen or cavity of a patient's body in order to aid in the positioning the distal end of the obturator 62, primary sheath 12 and/or secondary sheath 72 (including 82 and 92) in a position in close proximity to the stones or foreign bodies and the secondary sheath 70 may be used to guide additional irrigation, a catheter, a foreign body basket, a backstop, an instrument or device to the position in close proximity to the stones or foreign bodies simultaneously with the scope and/or irrigation, catheter, foreign body basket, backstop, instrument or device through the primary sheath 10.

The above method may further comprise the step of visualizing one or more stones and/or foreign objects which are too large to pass though the space between the scope and the inside surface of the primary sheath, but small enough to pass through the lumen of the primary 13, retracting the scope from the distal end of the sheath 12 to a point which is just proximal to the location within the proximal sheath where the side arm 30 emanates from the proximal sheath while visualizing the aspiration of the one or more stones and/or foreign objects up the sheath and into the side arm and collecting the stone, foreign body and/or fragments in the collection container.

Any method described herein may incorporate any design element contained within this application and any other document/application incorporated by reference herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention may be embodied in other forms without departing from the spirit and the essential attributes thereof, and, accordingly, reference should be made to the appended claims, rather than to the foregoing specification, as indicating the scope of the invention. The invention illustratively discloses herein suitably may be practiced in the absence of any element which is not specifically disclosed herein.

We claim:

1. A device for removing a stone, a stone fragment, or a foreign body from a patient comprising:
   a suction evacuation assembly which includes:
      a primary sheath which has a proximal end, a distal end, a lumen and an outer surface wherein the distal end is flexible, allowing the distal end to be actively or passively deflected;
      a handle chamber located at the proximal end of the primary sheath, the handle chamber including a proximal end, a distal end, a lumen, an arresting wall and a color band which is located on the outer surface;
      an obturator which is inserted into the proximal end of the primary sheath and which extends beyond the distal end of the sheath and is releaseably secured to the sheath;
      a side arm emanating from the outer surface of the primary sheath, the side arm having a lumen which opens into the lumen of the primary sheath, an outer surface and a pressure regulating mechanism (PRA) in the form of a slit or hole which passes from the outer surface of the side arm through to the lumen of the side arm;
         wherein when minimum negative pressure is required, the PRA is left open or minimally occluded and when additional negative pressure is required, the PRA is further or completely occluded;
      a deflection mechanism secured to the primary sheath which is operationally associated with the flexible, distal end which will enable the user to adjust the direction of the distal end of the sheath to aid with the direction of suction, irrigation, instrument placement, or removal of a stone, stone fragment or any other foreign body or tissue from a patient; and
      a secondary sheath which has a proximal end, a distal end and an outer surface, designed to be inserted into the primary sheath, the secondary sheath has a dual lumen with an oblong shape wherein the dual lumen allows passage of surgical instruments and irrigation fluid and wherein the oblong shape provides for adequate space for the egress of stone fragments and fluid through the primary and/or secondary sheath;
         wherein the secondary sheath further includes an insertion handle with a proximal end and a distal end and wherein the insertion handle is inserted into the handle chamber until the proximal end engages the arresting wall of the handle chamber to stabilize the secondary sheath when engaged within the primary sheath;
         wherein the distal end is flexible, allowing the distal end to be actively or passively deflected and wherein the secondary sheath is longer than the primary sheath allowing the distal end of the secondary sheath to extend beyond the distal end of the primary sheath in order to allow irrigation, a catheter, a foreign body basket, a backstop, an instrument or device to be passed to or beyond a stone, a stone fragment or other foreign body during a procedure to remove them; and
         wherein the obturator is withdrawn from the primary sheath and the secondary sheath is inserted into the primary sheath and into the patient in order to facilitate the removal of the stone, stone fragment or foreign body through the side arm for collection and examination.

2. The device of claim 1 further comprising:
   a proximal end of a primary tube releaseably secured to the side arm and a distal end of the primary tube releaseably secured to a collection container; and
   a proximal end of a secondary tube releaseably secured to the collection container and a distal end of the secondary tube releaseably secured to a negative pressure system;
      wherein the negative pressure system is activated in order to remove the stone or foreign body from the cavity if a diameter of the stone or foreign body is narrower than an inside diameter of the sheath and the side arm, or lithotripsy is performed on the stone or the foreign body in order to create fragments with a decreased diameter which allow the passage of the fragments within the inside diameter of the primary and/or secondary sheath and the side arm or in the space between the primary and secondary sheath and the side arm; and
      wherein the secondary sheath is withdrawn to just distal to the side arm to allow egress of stone, foreign body, or tissue fragments when such fragments are too large for the space between primary sheath and secondary sheath and the stone, foreign body and/or fragments are collected in the collection container.

3. The device of claim 1 wherein the primary sheath is comprised of a proximal sheath and a distal sheath wherein the distal sheath is separable from the proximal sheath and the proximal sheath is the same size or larger than the distal sheath.

4. The device of claim 3 wherein the distal sheath is made of a releasable, peelable material which may be peeled off of the distal sheath when no longer needed or wanted.

5. The device of claim 1 further comprises:
   an internally or externally expandable distal end of the primary sheath, that can be expanded to hold the sheath in place within the body cavity, or an anchoring mechanism operationally associated with the distal end of the sheath.

6. The device of claim 1 wherein the side arm further comprises a pressure regulating mechanism which allows a person using the suction evacuation assembly to increase or decrease the negative pressure within the suction evacuation assembly.

7. The device of claim 1 wherein the suction evacuation assembly further comprises
   a scope with a diameter which is smaller than an inner diameter of the primary sheath or either lumen of the secondary sheath of the suction evacuation assembly resulting in an open channel within the lumen of the primary sheath or secondary sheath which permits the passage of stones, pieces of stones or other foreign objects through the lumen of the primary sheath and through the side arm.

8. The device of claim 1 wherein the suction evacuation assembly further comprises an expansion mechanism located within the lumen of the primary sheath or on the obturator; and
an expandable, flexible distal end operationally associated with the expansion mechanism;
wherein the distal end of the primary sheath is introduced into a smaller cross section and located into a desired position or orientation at which time the expansion mechanism is activated and expanded which expands the flexible distal end of the sheath, creating a larger cross section through internal expansion.

9. The device of claim 1 wherein the suction evacuation assembly further comprising
one or more holes located near a handle of the primary sheath, wherein the holes extend from the outer surface of the primary sheath through to the lumen of the primary sheath and allow for the draining/evacuation of urine or any other fluid from a patient during a procedure.

10. The device of claim 1 wherein the dual lumen within the secondary sheath each have a proximal end and a distal end which are joined to one another at the distal end and are separated from one another at the proximal end.

11. The device of claim 1 wherein the obturator further includes, a central lumen which may accommodate a tool, such as a guide wire or needle, an expandable distal end of the obturator, such as a balloon that can be inflated to hold the obturator in place within a patient, or an anchoring mechanism operationally associated with the distal end of the obturator.

12. The device of claim 1 further comprises an accessory channel secured to the outer surface of the primary sheath, the accessory channel includes a proximal end with a connector and a distal end located in the proximity of the distal end of the primary sheath.

13. A method for removing a stone, a stone fragment or a foreign body from a patient using a suction evacuation assembly comprising the steps of:
providing a suction evacuation assembly which includes:
a primary sheath which has a proximal end, a distal end and an outer surface wherein the distal end is flexible, allowing the distal end to be actively or passively deflected;
a handle chamber located at the proximal end of the primary sheath, the handle chamber including a proximal end, a distal end, a lumen, an arresting wall and a color band which is located on the outer surface;
an obturator which is inserted into the proximal end of the sheath and which extends beyond the distal end of the sheath and is releaseably secured to the sheath;
a side arm emanating from the outer surface of the primary sheath, the side arm having a lumen which opens into the lumen of the primary sheath, an outer surface and a pressure regulating mechanism (PRA) in the form of a slit or hole which passes from the outer surface of the side arm through to the lumen of the side arm;
wherein when minimum negative pressure is required, the PRA is left open or minimally occluded and when additional negative pressure is required, the PRA is further or completely occluded;
a deflection mechanism secured to the primary sheath which is operationally associated with the flexible, distal end which will enable the user to adjust the direction of the distal end of the sheath to aid with the direction of suction, irrigation, instrument placement, or removal of a stone, stone fragment or any other foreign body or tissue from a patient; and
a secondary sheath which has a proximal end, a distal end and an outer surface, designed to be inserted into the primary sheath, the secondary sheath has a dual lumen with an oblong shape wherein the dual lumen allows passage of surgical instruments and irrigation fluid and wherein the oblong shape provides for adequate space for the egress of stone fragments and fluid through the primary and/or secondary sheath;
wherein the secondary sheath further includes an insertion handle with a proximal end and a distal end and wherein the insertion handle is inserted into the handle chamber until the proximal end engages the arresting wall of the handle chamber to stabilize the secondary sheath when engaged within the primary sheath;
wherein the distal end is flexible, allowing the distal end to be actively or passively deflected and wherein the secondary sheath is longer than the primary sheath allowing the distal end of the secondary sheath to extend beyond the distal end of the primary sheath in order to allow irrigation, a catheter, a foreign body basket, a backstop, an instrument or device to be passed to or beyond a stone, a stone fragment or other foreign body during a procedure to remove them;
inserting an obturator into the proximal end of the primary sheath which extends beyond the distal end of the primary sheath and releaseably securing the obturator to the sheath;
inserting the distal end of the primary sheath into a patient's body containing one or more stones or foreign bodies;
positioning the distal ends of the primary sheath and the obturator in a position in close proximity to the stones or foreign bodies;
disengaging the obturator from the proximal end of the primary sheath and removing the obturator from the primary sheath;
the insertion handle is inserted into the handle chamber until the proximal end engages the arresting wall of the handle chamber to stabilize the secondary sheath
inserting the secondary sheath into the proximal end of the primary sheath and extending the distal end of the secondary sheath beyond the distal end of the primary sheath and inserting the insertion handle into the handle chamber until the proximal end engages the arresting wall of the handle chamber to stabilize the secondary sheath releaseably securing the secondary sheath to the primary sheath;
connecting one end of a primary tube to the side arm and connecting the other end of the primary tube to a collection bottle;
connecting one end of a secondary tube to the collection bottle and connecting the other end of the secondary tube to a negative pressure system;
inserting a scope into either the primary sheath or the secondary sheath and into the patient;
adjusting the direction of the deflectable tip of the distal end of the primary and secondary sheaths using the deflection mechanism;
visualizing the stone or foreign body using the scope;
activating the negative pressure system in order to remove the stone or foreign body from the cavity if a diameter of the stone or foreign body is narrower than an inside diameter of the sheath and the side arm, or performing a lithotripsy on the stone or the foreign body in order to create fragments with a decreased diameter which allow the passage of the fragments within the inside diameter of the sheath and the side arm; and collecting the stone, foreign body and/or fragments through the side arm in the collection bottle.

14. The method of claim 13 wherein the primary sheath is comprised of a proximal sheath and a distal sheath wherein the distal sheath is separable from the proximal sheath and the proximal sheath is the same size or larger than the distal sheath.

15. The method of claim 14 wherein the distal sheath is made of a releasable, peelable material which may be peeled off of the distal sheath when no longer needed or wanted.

16. The method of claim 13 further comprising the step of:

visualizing one or more stones and/or foreign objects which are too large to pass though the space between the scope and the inside surface of the primary or secondary sheath, but small enough to pass through the lumen of the primary or secondary sheath;

retracting the scope from the distal end of the sheath to a point which is just proximal to the location within the proximal sheath where the side arm emanates from the proximal sheath while visualizing the aspiration of the one or more stones and/or foreign objects up the sheath and into the side arm; and collecting the stone, foreign body and/or fragments in the collection container.

17. The method of claim 13 further comprising:

an internally or externally expandable distal end of the primary sheath, such as a balloon or other expanding means that can be expanded to hold the sheath in place within the body cavity, or an anchoring mechanism operationally associated with the distal end of the sheath.

18. The method of claim 13 wherein the side arm further comprises a pressure regulating mechanism which allows a person using the suction evacuation assembly to increase or decrease the negative pressure within the suction evacuation assembly.

19. The method of claim 13 wherein the suction evacuation assembly further comprises one or more holes located near a handle of the primary sheath, wherein the holes extend from the outer surface of the primary sheath through to the lumen of the primary sheath and allow for the draining/evacuation of urine or any other fluid from a patient during a procedure.

20. The method of claim 13 wherein the dual lumen within the secondary sheath each have a proximal end and a distal end which are joined to one another at the distal end and are separated from one another at the proximal end.

21. The method of claim 13 wherein the obturator further includes, a central lumen which may accommodate a tool, such as a guide wire or needle, an expandable distal end of the obturator, such as a balloon that can be inflated to hold the obturator in place within a patient, or an anchoring mechanism operationally associated with the distal end of the obturator.

22. The method of claim 13 wherein the suction evacuation assembly further comprises an accessory channel secured to the outer surface of the primary sheath, the accessory channel includes a proximal end with a connector and a distal end located in the proximity of the distal end of the primary sheath.

23. The method of claim 13 wherein the suction evacuation assembly further comprises an expansion mechanism located within the lumen of the primary sheath or on the obturator; and an expandable, flexible distal end operationally associated with the expansion mechanism;

wherein the distal end of the primary sheath is introduced into a smaller cross section and located into a desired position or orientation at which time the expansion mechanism is activated and expanded which expands the flexible distal end of the sheath, creating a larger cross section through internal expansion.

* * * * *